(12) United States Patent
Takahashi et al.

(10) Patent No.: US 11,529,281 B2
(45) Date of Patent: Dec. 20, 2022

(54) GAIT MOTION ASSISTING APPARATUS

(71) Applicants: Suncall Corporation, Kyoto (JP);
Kyoto University, Kyoto (JP);
National University Corporation Kyoto Institute of Technology, Kyoto (JP)

(72) Inventors: Rei Takahashi, Kyoto (JP); Yukinobu Makihara, Tokyo (JP); Tadao Tsuboyama, Kyoto (JP); Koji Ohata, Kyoto (JP); Yuichi Sawada, Kyoto (JP); Yoshiyuki Higashi, Kyoto (JP)

(73) Assignees: Suncall Corporation, Kyoto (JP);
Kyoto University, Kyoto (JP);
National University Corporation Kyoto institute of Technology, Kyoto (JP)

( * ) Notice: Subject to any disclaimer, the term of this patent is extended or adjusted under 35 U.S.C. 154(b) by 277 days.

(21) Appl. No.: 16/772,430

(22) PCT Filed: Nov. 5, 2018

(86) PCT No.: PCT/JP2018/040984
§ 371 (c)(1),
(2) Date: Jun. 12, 2020

(87) PCT Pub. No.: WO2019/116779
PCT Pub. Date: Jun. 20, 2019

(65) Prior Publication Data
US 2021/0085552 A1 Mar. 25, 2021

(30) Foreign Application Priority Data
Dec. 15, 2017 (JP) .............................. JP2017-240288

(51) Int. Cl.
*A61H 3/00* (2006.01)
*A61F 5/01* (2006.01)

(52) U.S. Cl.
CPC ............. *A61H 3/00* (2013.01); *A61F 5/0123* (2013.01); *A61H 2003/007* (2013.01);
(Continued)

(58) Field of Classification Search
CPC . A61F 5/00; A61F 5/0123; A61H 2201/1671; A61H 2201/5097;
(Continued)

(56) References Cited

U.S. PATENT DOCUMENTS

2015/0366738 A1* 12/2015 Endo ...................... G05B 15/02
482/4
2016/0058646 A1 3/2016 Seo et al.

FOREIGN PATENT DOCUMENTS

JP 2009-213671 A 9/2009
JP 5386253 B2 1/2014
(Continued)

OTHER PUBLICATIONS

Supplementary European Search Report in EP Application No. 18 88 9809 dated Sep. 1, 2021, 8 pages.
(Continued)

*Primary Examiner* — Ophelia A Hawthorne
(74) *Attorney, Agent, or Firm* — Sterne, Kessler, Goldstein & Fox P.L.L.C.

(57) ABSTRACT

A gait motion assisting apparatus of the present invention includes an actuator unit controlling driver so that assisting force calculated by applying gait motion timing based on detected thigh phase angle to output pattern saved data is imparted to lower leg, and a terminal device capable of wireless-communicating with control device of the actuator unit. The terminal device can receive assisting force setting (Continued)

value including assisting force imparting period during gait cycle and create, based on the assisting force setting value, output pattern setting data indicating a relationship between the gait motion timing and a size of assisting force to be imparted to the lower leg. The control device is configured to overwrite-save the output pattern setting data received from the terminal device as the output pattern saved data.

10 Claims, 20 Drawing Sheets

(52) U.S. Cl.
CPC ........... *A61H 2201/1652* (2013.01); *A61H 2201/1671* (2013.01); *A61H 2201/5043* (2013.01); *A61H 2201/5097* (2013.01); *A61H 2205/088* (2013.01); *A61H 2205/102* (2013.01)

(58) Field of Classification Search
CPC ........ A61H 2205/088; A61H 2205/102; A61H 2201/1652; A61H 2201/5043; A61H 2003/007; A61H 3/00; A61H 2201/5069; B25J 11/00

See application file for complete search history.

(56) References Cited

FOREIGN PATENT DOCUMENTS

| | | | |
|---|---|---|---|
| JP | 2015-058033 | A | 3/2015 |
| JP | 5724312 | B2 | 5/2015 |
| JP | 5799608 | B2 | 10/2015 |
| JP | 2016-002408 | A | 1/2016 |
| JP | 2017-213246 | A | 12/2017 |
| JP | 2017-213347 | A | 12/2017 |
| WO | 2012/100250 | A1 | 7/2012 |

OTHER PUBLICATIONS

International Search Report issued in Japanese Application No. PCT/JP2018/040984, dated Jan. 15, 2019, 5 pages.

\* cited by examiner

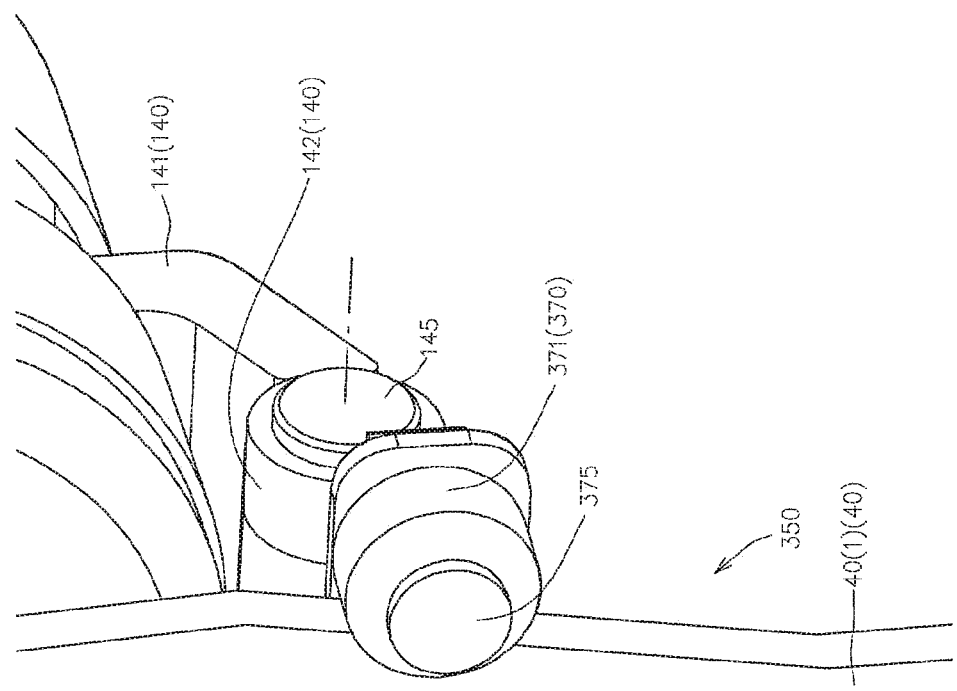
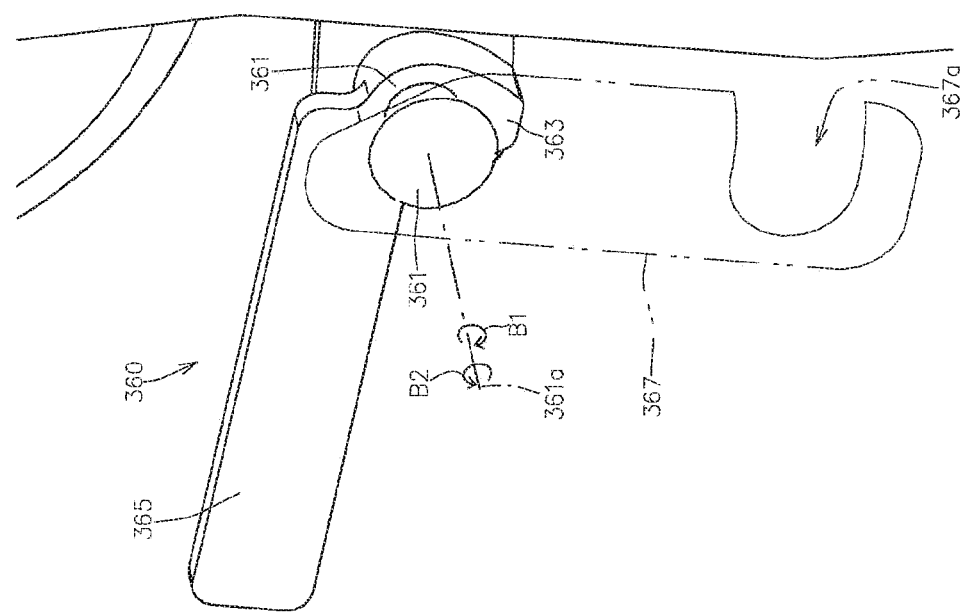
FIG.15

GAIT MOTION ASSISTING APPARATUS

FIELD OF THE INVENTION

The present invention relates to a gait motion assisting apparatus imparting gait assisting force to a user that wears a knee-ankle-foot orthosis.

BACKGROUND ART

Knee-ankle-foot orthoses for supporting a knee joint are utilized as gait assistance or rehabilitation devices for people with leg disability or people with paralysis due to a stroke or the like, and actuator-equipped knee ankle foot orthoses are also proposed that are equipped with an actuator unit including a driver such as an electric motor for assisting movement of a leg (see Patent Literatures 1 to 3 below).

Specifically, conventional actuator-equipped knee ankle foot orthoses include a thigh-side brace to be attached to a user's thigh, a lower leg-side brace to be attached to the user's lower leg and connected to the thigh-side brace so as to be rotatable around the user's knee joint, an actuator attached to the thigh-side brace and capable of imparting assisting force around the knee joint to the lower leg-side brace, a lower leg angle sensor for detecting the rotational angle of the lower leg around the knee joint relative to the thigh, and a control device responsible for operational control for the actuator, wherein the control device is configured to execute operational control for the actuator based on a detection signal from the lower leg angle sensor.

That is, the above conventional actuator-equipped knee ankle foot orthoses detect movement of the lower leg (the angle of the lower leg around the knee joint relative to the thigh), which is a control target site to which an assisting force is to be imparted by the actuator, by means of the lower leg angle sensor, and perform operational control for the actuator such that assisting force having a size and a direction calculated based on movement of the lower leg is imparted to the lower leg.

However, in the case of paralysis due to a stroke or the like, gait motion of the lower leg (forward and backward swing motion of the lower leg around the knee joint) often cannot be performed normally, while gait motion of the thigh (forward and backward swing motion of the thigh around the hip joint) can be performed relatively normally.

In such a case, since the above conventional actuator-equipped knee ankle foot orthoses perform operational control for the actuator based on movement of the lower leg that is incapable of normal gait motion, there is a possibility that suitable gait assisting force cannot be provided.

As another gait assisting device, proposed is a gait assisting device that includes an imparting unit for imparting assisting force, a control unit for performing operational control for the imparting unit, a detection unit for detecting at least one of a hip joint angle and a hip joint angular velocity, and a calculation unit for calculating the phase angle of the thigh based on a detection result of the detection unit, and that is configured such that the control unit performs operational control for the imparting unit based on the phase angle (see Patent Literature 4 below).

However, the gait assisting device of Patent Literature 4 also detects movement of a control target site (thigh) to which assisting force is to be imparted and performs operational control for the imparting unit that imparts assisting force to the thigh, which is the control target site, based on a detection result, and is thus based on the same technical idea as the actuator-equipped knee ankle foot orthoses described in Patent Literatures 1 to 3.

Meanwhile, a gait cycle includes a heel contact phase including a heel contact time point when the heel contacts the ground in front of a vertical axis line that passes through the hip joint (a period when the forward-raised foot contacts the floor), a stance phase when the heel-contacted leg after heel contact is relatively moved backward while being in contact with the ground (a period when the floor-contacted lower limb is relatively moved backward relative to the body), and a swing phase when the leg contacting the ground since the end of stance phase is raised and relatively moved forward.

Here, which timing during gait cycle becomes the heel contact phase, the stance phase, or the swing phase is different for each user and, even for the same user, is different depending on the extent of recovery.

Accordingly, it is preferable that the timing of imparting, and the size of, assisting force by the actuator (or the imparting unit) can be easily changed according to the current state of a user who is using the apparatus, and none of the patent documents sufficiently take this point into consideration.

PRIOR ART DOCUMENT

Patent Literature

Patent Literature 1: JP 5724312B
Patent Literature 2: JP 5799608B
Patent Literature 3: JP 5386253B
Patent Literature 4: JP 2016-002408A

SUMMARY OF THE INVENTION

The present invention has been conceived in view of such conventional art, and an object of the present invention is to provide a gait motion assisting apparatus that can be attached to a knee-ankle-foot orthosis wherein a lower leg-side brace is connected to a thigh-side brace so as to be rotatable around a brace-side pivot axis line and that includes an actuator unit capable of imparting assisting force around the brace-side pivot axis line to the lower leg-side brace, wherein the gait motion assisting apparatus is capable of imparting gait assisting force corresponding to the gait state during gait cycle to a lower leg even for a user having difficulty in performing normal gait motion of the lower leg and, moreover, enables the imparting timing of gait assisting force imparted to the lower leg during gait cycle to be easily changed as desired.

In order to achieve the object, the present invention provides a gait motion assisting apparatus including a terminal device and an actuator unit removably attachable to a knee ankle foot orthosis having a thigh-side brace and a lower leg-side brace to be respectively attached to a user's thigh and lower leg wherein the lower leg-side brace is connected to the thigh-side brace so as to be rotatable around a brace-side pivot axis line, wherein the actuator unit has an upper frame and a lower frame respectively connectable to the thigh-side brace and the lower leg-side brace, an actuator-side rotational connecting part for connecting both frames such that the lower frame is rotatable around an actuator-side pivot axis line relative to the upper frame, a driver attached to the upper frame to produce driving force for rotating the lower frame around the actuator-side pivot axis line, a thigh orientation detecting means capable of detecting an angle-related signal relating to a hip joint angle that is a front-back swing angle of the user's thigh, and an actuator-side control device responsible for operational control for the driver; the actuator-side control device is configured to calculate, based on the angle-related signal at a sampling timing, a thigh phase angle at the sampling timing, calculate, based on the thigh phase angle, a gait motion timing during gait cycle corresponding to the sampling timing, apply the gait motion timing of the sampling timing to output pattern saved data that is saved in the actuator-side control device and that indicates a relationship between a gait motion timing during gait cycle and a size of assisting force to be imparted to the lower frame to calculate assisting force to be imparted to the lower frame at the sampling timing, and execute operational control for the driver such that the assisting force is output; the terminal device has a display part, an input part, a terminal-side control part, and a wireless communication part for performing wireless communication with the actuator-side control device, and is capable of receiving via the input part an assisting force setting value including an assisting force imparting period obtained by specifying a period for imparting assisting force to the lower frame by using a gait motion timing during gait cycle; the terminal-side control part creates, based on the assisting force setting value received via the input part, output pattern setting data indicating a relationship between a gait motion timing during gait cycle and a size of assisting force to be imparted to the lower frame, and sends the output pattern setting data to the actuator-side control device via the wireless communication part according to manual send operation via the input part; and the actuator-side control device overwrite-saves the output pattern setting data received from the terminal device as the output pattern saved data.

Since the gait motion assisting apparatus according to the present invention includes the actuator unit removably attachable to the knee-ankle-foot orthosis and the terminal device separate from and capable of wireless-communicating with the actuator unit, wherein the actuator unit is configured to calculate, based on the angle-related signal relating to the hip joint angle at a sampling timing, a thigh phase angle at the sampling timing, calculate, based on the thigh phase angle, a gait motion timing during gait cycle, apply the gait motion timing to output pattern saved data that is saved in advance to calculate assisting force to be imparted to the lower frame at the sampling timing, and execute operational control for the driver such that the assisting force is output, the gait motion assisting apparatus makes it possible to impart gait assisting force corresponding to the gait state during gait cycle to the lower leg even for a user having difficulty in performing normal gait motion of the lower leg.

Moreover, since, the terminal device in the gait motion assisting apparatus according to the present invention is configured to be capable of receiving an assisting force setting value including an assisting force imparting period obtained by specifying a period for imparting assisting force to the lower frame by using the gait motion timing during gait cycle, create, based on the assisting force setting value, output pattern setting data indicating a relationship between the gait motion timing and a size of assisting force to be imparted to the lower frame, and send the output pattern setting data to the actuator-side control device in the actuator unit according to manual send operation, and the actuator-side control device is configured to overwrite-save the output pattern setting data received from the terminal device as the output pattern saved data, the gait motion assisting apparatus makes it possible to easily change the imparting timing of gait assisting force imparted to the lower leg during gait cycle as desired.

In one embodiment, the assisting force imparting period is a period defined by an assisting force start timing and an assisting force end timing specified in percentage relative to a gait cycle under a condition where a preset reference gait motion timing during gait cycle is regarded as a zero point.

In this case, the output pattern setting data is data indicating a relationship between percentage of a gait motion timing relative to a gait cycle in a state where the reference gait motion timing is regarded as a zero point and a size of assisting force to be imparted to the lower frame.

In a preferable configuration, the terminal device is configured to be capable of receiving via the input part a size of assisting force to be imparted during the assisting force imparting period in addition to the assisting force imparting period as the assisting force setting value.

In the preferable configuration, the size of assisting force that can be input as the assisting force setting value may include an output value specified in percentage relative to a predetermined reference output value of the driver and an output direction of the driver indicating a rotational direction of the lower frame around the actuator-side pivot axis line.

In the preferable configuration, the terminal-side control part may store a plurality of waveform patterns of assisting force to be output by the driver, and the terminal device may enable one waveform pattern to be selected from the plurality of waveform patterns via the input part.

In this case, the assisting force setting value includes the waveform pattern selected via the input part.

In a preferable embodiment, the terminal-side control part is configured to divide-manage a gait cycle into a preset number n (n is an integer of 2 or greater) of output setting periods, and the terminal device is capable of receiving an assisting force setting value for each of the n output setting periods via the input part.

In a more preferable embodiment, the terminal device enables one or a plurality of output setting periods in which the assisting force setting value is reflected in the output pattern setting data to be selected from the n output setting periods via the input part.

In a preferable embodiment, the display part is configured to have an input key display area for displaying an input key for performing manual operation and a data display area for displaying a graph of the output pattern setting data.

In a more preferable embodiment, the terminal-side control part is configured to read output pattern saved data from the actuator-side control device via the wireless communication part according to manual read operation via the input part, and display a graph of the output pattern saved data as output pattern setting data in the data display area.

In a preferable embodiment, the terminal device is a tablet terminal including a touch panel acting as the display part and the input part.

BRIEF DESCRIPTION OF THE DRAWINGS

FIG. 15 is a cross-sectional perspective view corresponding to FIG. 13, and shows a state where a lower fastening member is positioned in a released position.

EMBODIMENT FOR CARRYING OUT THE INVENTION

Below, one embodiment of the gait motion assisting apparatus according to the present invention will now be described with reference to the attached drawings.

The gait motion assisting apparatus according to the present embodiment impart gait assisting force to a user wear a knee-ankle-foot orthosis 1, and includes an actuator unit 100 detachably attached to the knee-ankle-foot orthosis 1 and a terminal device 600 separate from the actuator unit 100 and capable of performing wireless communication with the actuator unit 100.

Figure 1:
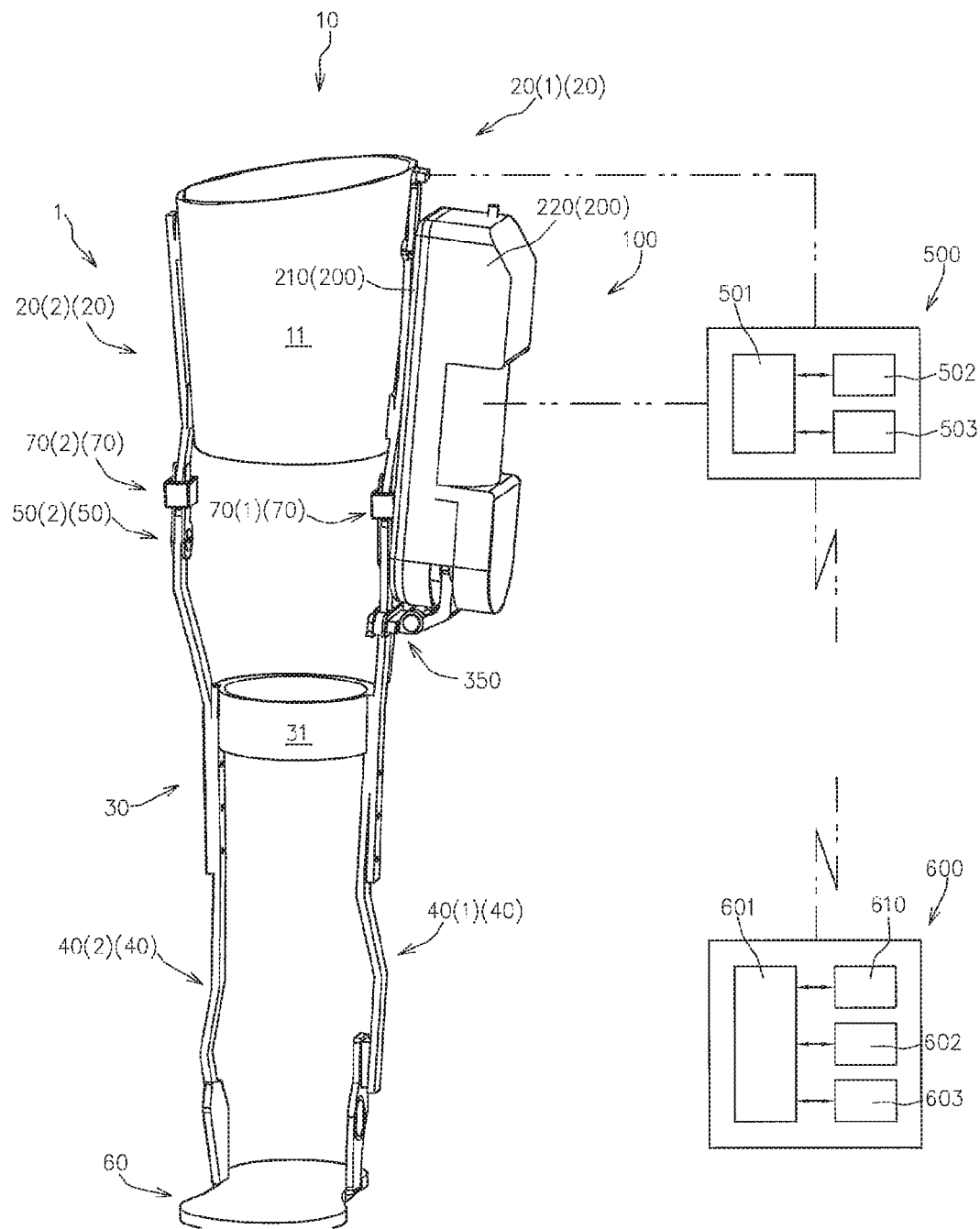
FIG. 1 is a schematic view of a gait motion assisting apparatus according to an embodiment of the present invention, and show a state in which an actuator unit in the gait motion assisting apparatus is attached to a knee-ankle-foot orthosis.

FIG. 1 is a schematic view of the gait motion assisting apparatus, and shows a state where the actuator unit 100 is attached to the knee-ankle-foot orthosis 1.

Figure 2:
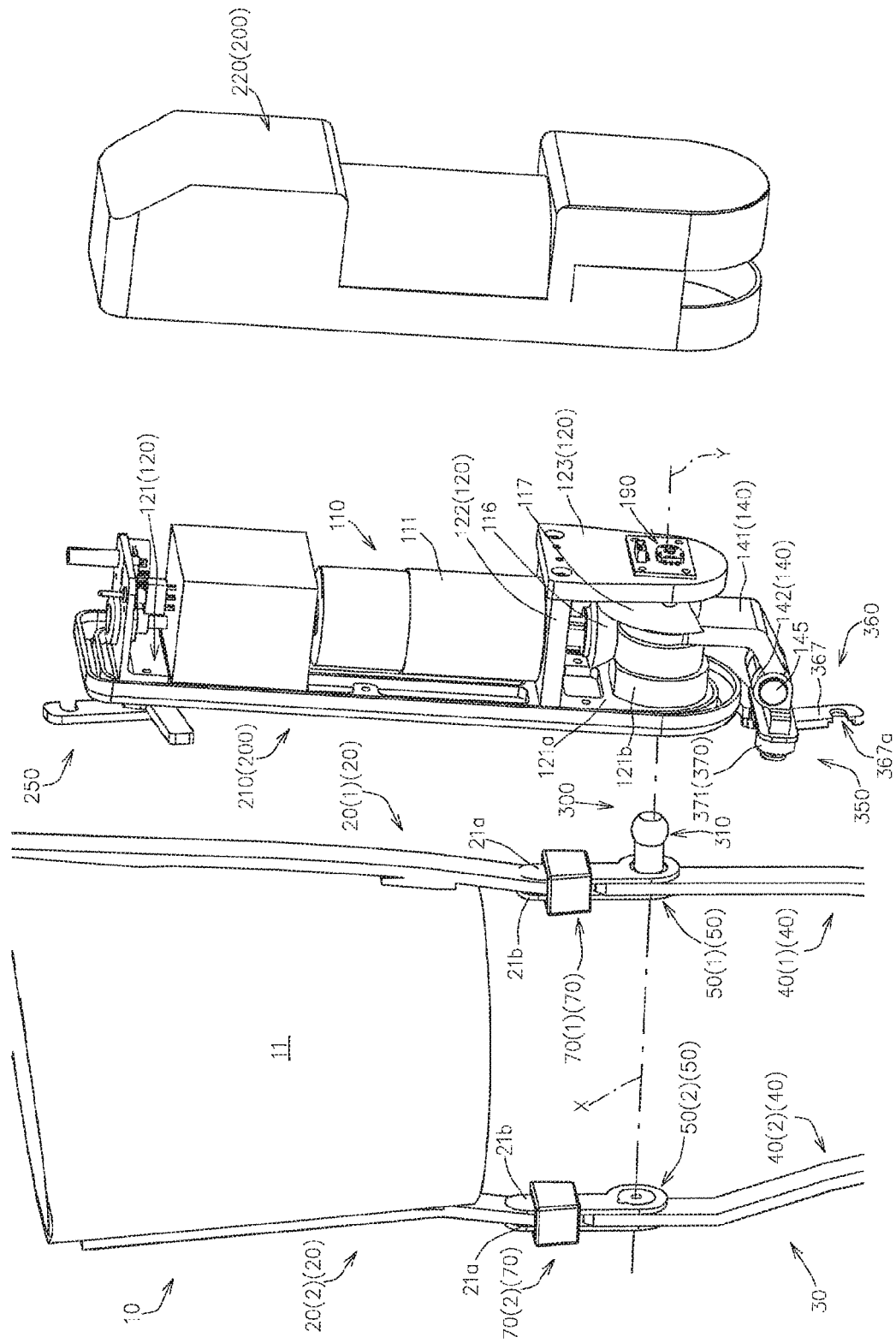
FIG. 2 is a partially exploded perspective view of the actuator unit shown in FIG. 1 and shows a state viewed from the outer side in the user width direction.
Figure 3:
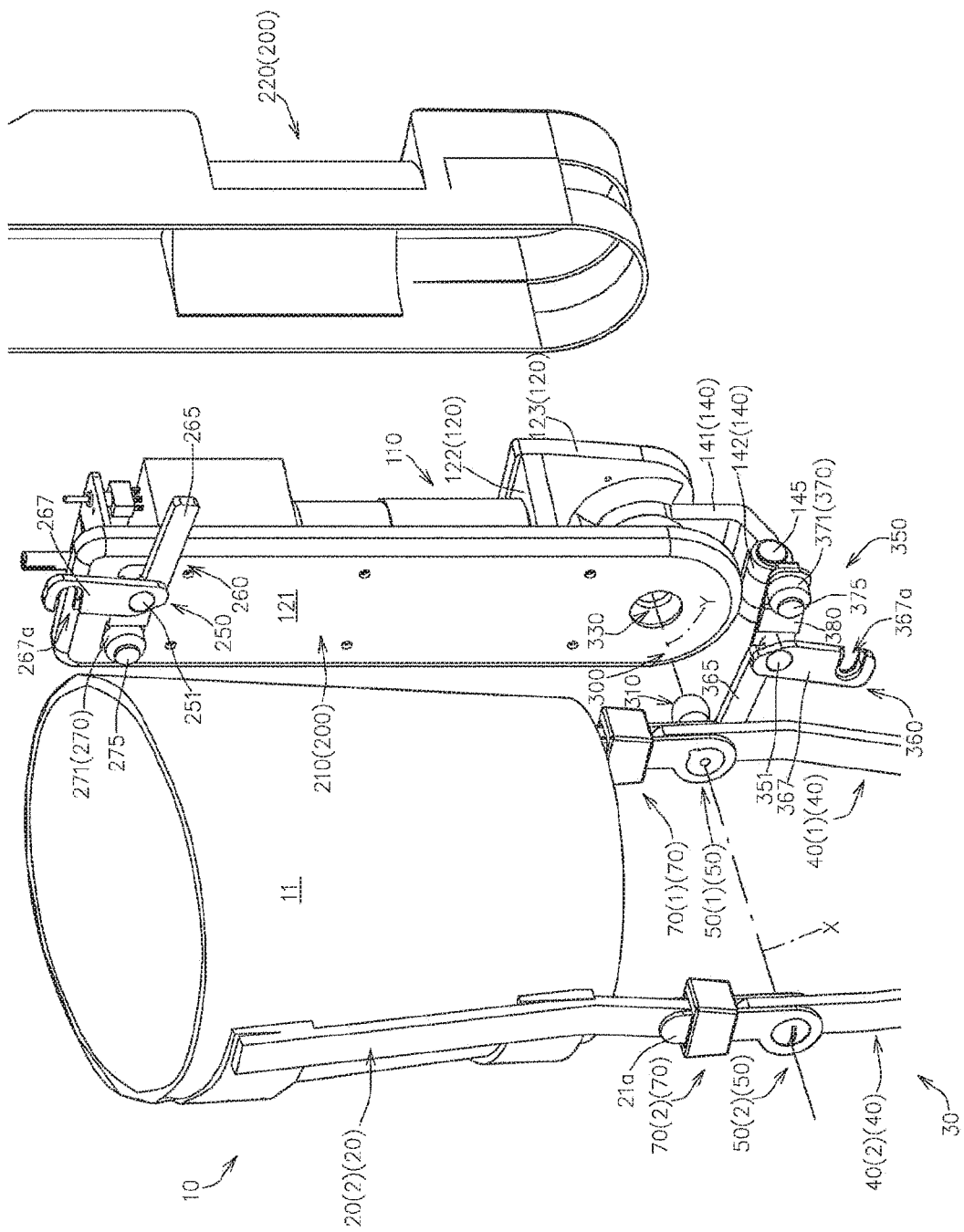
FIG. 3 is a partially exploded perspective view of the actuator unit shown in FIG. 1 and shows a state viewed from the inner side in the user width direction.

FIGS. 2 and 3 respectively show partially exploded perspective views of the actuator unit 100 as viewed from the outer side and the inner side in the user width direction.

First, the configuration of the knee-ankle-foot orthosis 1 will now be described.

The knee-ankle-foot orthosis 1 is a device to be worn by a person with leg disability or a person with paralysis due to a stroke or the like for gait assistance or for rehabilitation, and is custom-made according to the user's physique.

As shown in FIGS. 1 to 3, the knee-ankle-foot orthosis 1 has a thigh-side brace 10 and a lower leg-side brace 30 to be respectively attached to the user's thigh and lower leg, wherein the lower leg-side brace 30 is connected to the thigh-side brace 10 so as to be rotatable around a brace-side pivot axis line X relative to the thigh-side brace 10.

The thigh-side brace 10 includes a thigh attachment 11 to which the user's thigh is attached and a thigh frame 20 supporting the thigh attachment 11.

The lower leg-side brace 30 includes a lower leg attachment 31 to which the user's lower leg is attached and a lower leg frame 40 supporting the lower leg attachment 31.

The thigh attachment 11 and the lower leg attachment 31 may take various forms as long as they are respectively attachable to the user's thigh and lower leg.

In the present embodiment, as shown in FIG. 1, the thigh attachment 11 is in a cylindrical form having an attachment hole with such a size that the user's thigh can be inserted and the thigh attachment 11 fits the thigh.

Likewise, the lower leg attachment 31 is in a cylindrical form having an attachment hole with such a size that the user's lower leg can be inserted and the lower leg attachment 31 fits the lower leg.

As shown in FIGS. 1 to 3, the thigh frame 20 has a first thigh frame 20(1) vertically extending along the user's thigh on the outer side in the user width direction.

In the present embodiment, as shown in FIGS. 1 to 3, the thigh frame 20 further has a second thigh frame 20(2) vertically extending along the user's thigh on the inner side in the user width direction so as to be opposed to the first thigh frame 20(1), with the user's thigh inserted in the thigh attachment 11 in-between.

As shown in FIGS. 1 to 3, the lower leg frame 40 has a first lower leg frame 40(1) vertically extending along the user's lower leg on the outer side in the user width direction.

In the present embodiment, as shown in FIGS. 1 to 3, the lower leg frame 40 further has a second lower leg frame 40(2) vertically extending along the user's lower leg on the inner side in the user width direction so as to be opposed to the first lower leg frame 40(1), with the user's lower leg inserted in the lower leg attachment 31 in-between.

Figure 4:
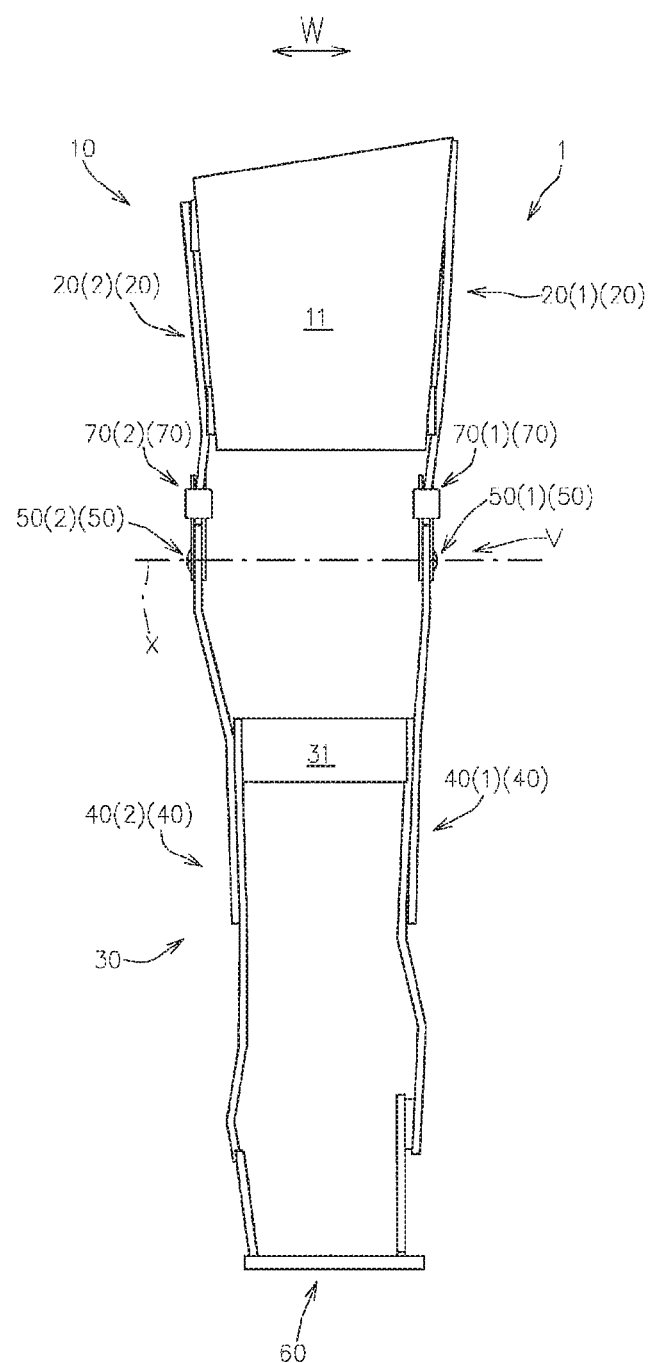
FIG. 4 is a front view of the knee-ankle-foot orthosis alone in a state where the actuator unit is removed.

FIG. 4 shows a front view of the knee-ankle-foot orthosis 1 alone.

As described above, the thigh frame 20 and the lower leg frame 40 are custom-made according to a user so as to extend along the user's thigh and lower leg, respectively.

That is, the tilt angle and/or the curvature with respect to a user width direction W of the thigh frame 20 relative to the lower leg frame 40 is different for each knee-ankle-foot orthosis that is custom-made according to the user's physique.

In the present embodiment, as shown in FIGS. 1 and 4, the knee-ankle-foot orthosis 1 further has a foot frame 60 on which a user places a foot.

In this case, the lower end part of the lower leg frame 40 is connected to the foot frame 60.

Figure 5:
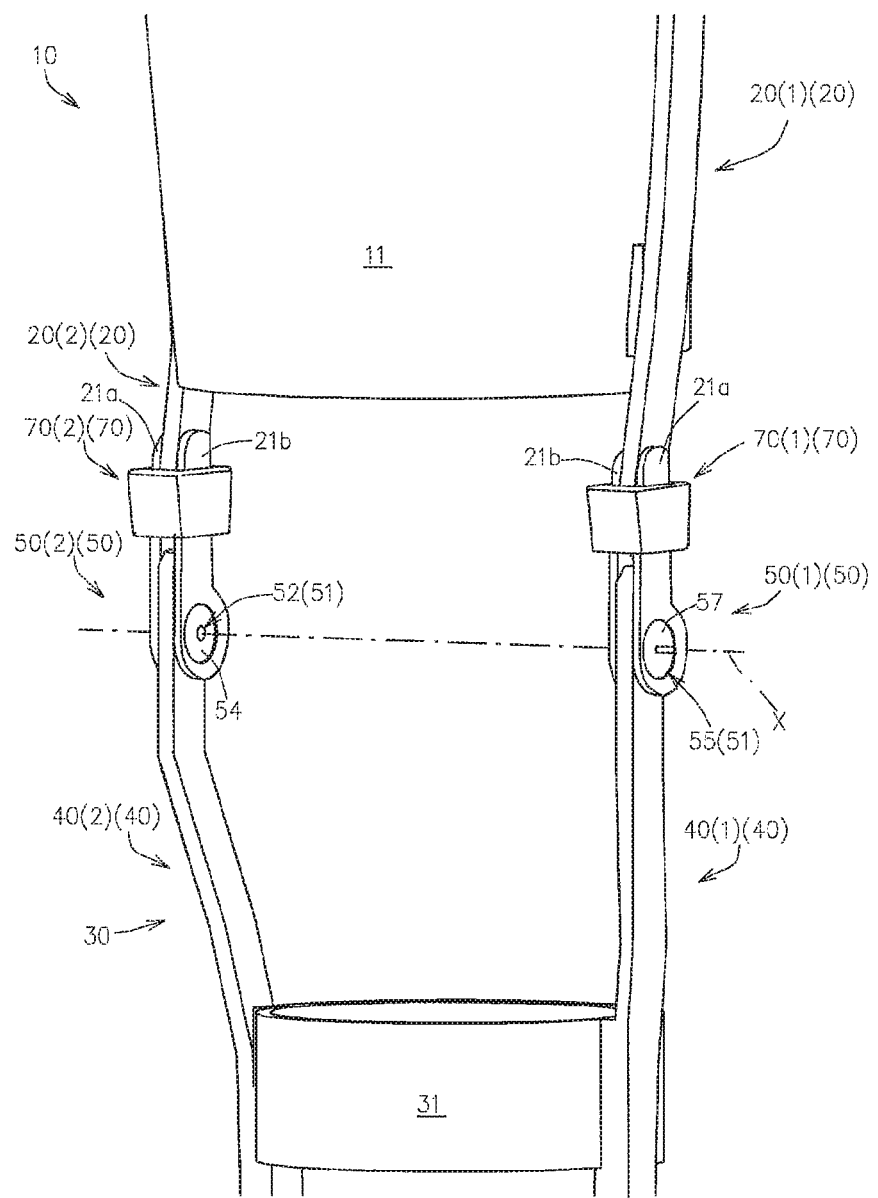
FIG. 5 is a perspective view of V part in FIG. 4.

FIG. 5 shows a perspective view of the V part in FIG. 4.

The knee-ankle-foot orthosis 1 further has a brace-side rotational connecting part 50.

The brace-side rotational connecting part 50 connects the thigh frame 20 and the lower leg frame 40 such that the lower leg frame 40 is rotatable relative to the thigh frame 20 around the brace-side pivot axis line X that is coaxial with the swing axis line of the user's knee joint.

As described above, in the present embodiment, the thigh-side brace 10 has the first and second thigh frames 20(1), 20(2), and the lower leg-side brace 30 has the first and second lower leg frames 40(1), 40(2).

Accordingly, as shown in FIGS. 1 to 5, the brace-side rotational connecting part 50 has a first brace-side rotational connecting part 50(1) for connecting the first thigh frame 20(1) and the first lower leg frame 40(1) positioned on the outer side in the user width direction so as to be rotatable around the brace-side pivot axis line X, and a second brace-side rotational connecting part 50(2) for connecting the second thigh frame 20(2) and the second lower leg frame 40(2) positioned on the inner side in the user width direction so as to be rotatable around the brace-side pivot axis line X.

Figure 6:
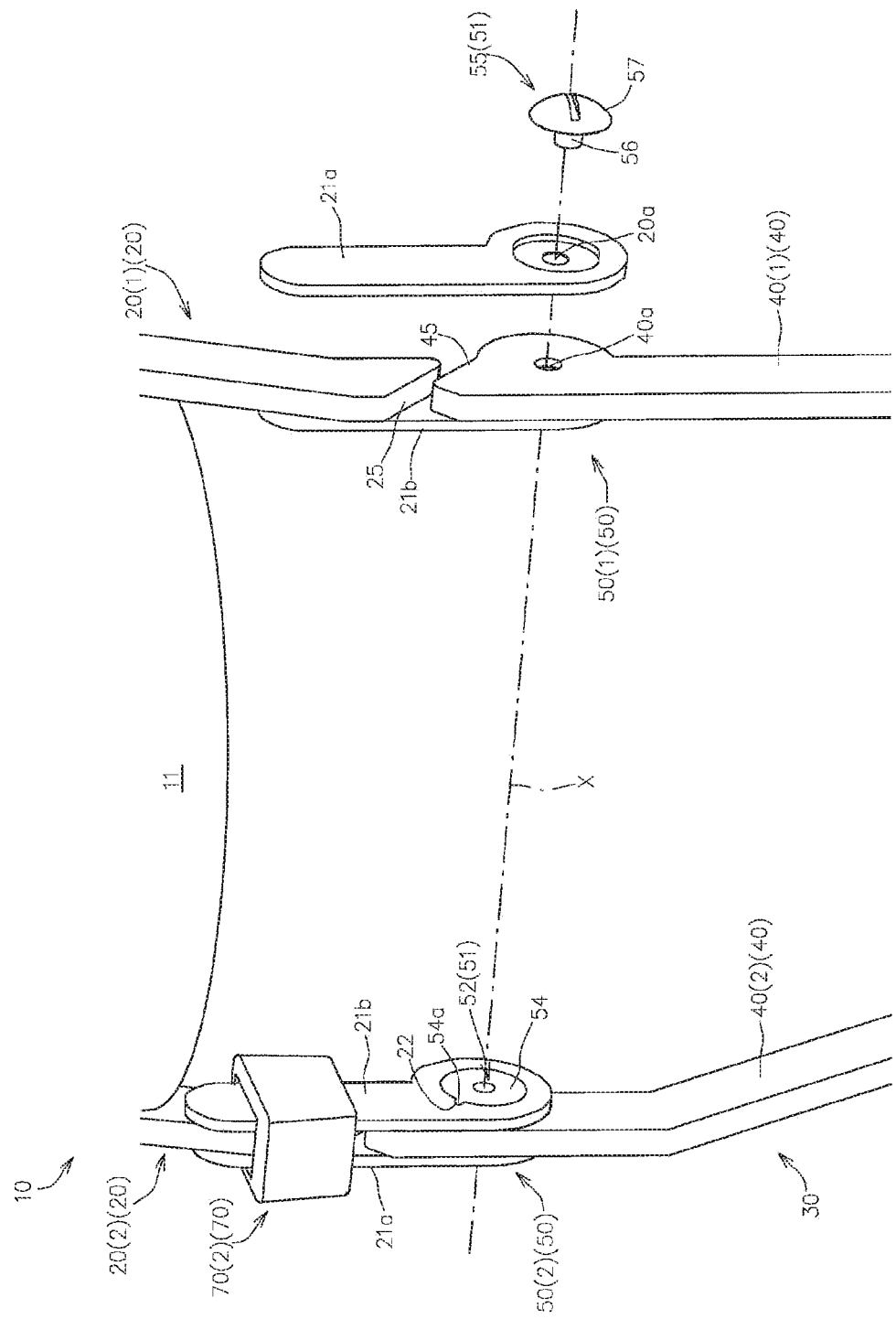
FIG. 6 is an enlarged perspective view of FIG. 5 in which a first connecting piece of a first thigh frame in the knee-ankle-foot orthosis that is positioned on an outer side in the user width direction and an externally threaded member of a first brace-side rotational connecting part that is positioned on an outer side in the user width direction are disassembled.

FIG. 6 shows an enlarged perspective view of FIG. 5 in a state where a first connecting piece 21a, which will be described below, of the first thigh frame 20(1) and an externally threaded member 55, which will be described below, of the first brace-side rotational connecting part 50(1) in FIG. 5 are disassembled.

In FIG. 6, illustration of a first locking member 70(1), which will be described below, is omitted for easier understanding.

Figure 7:
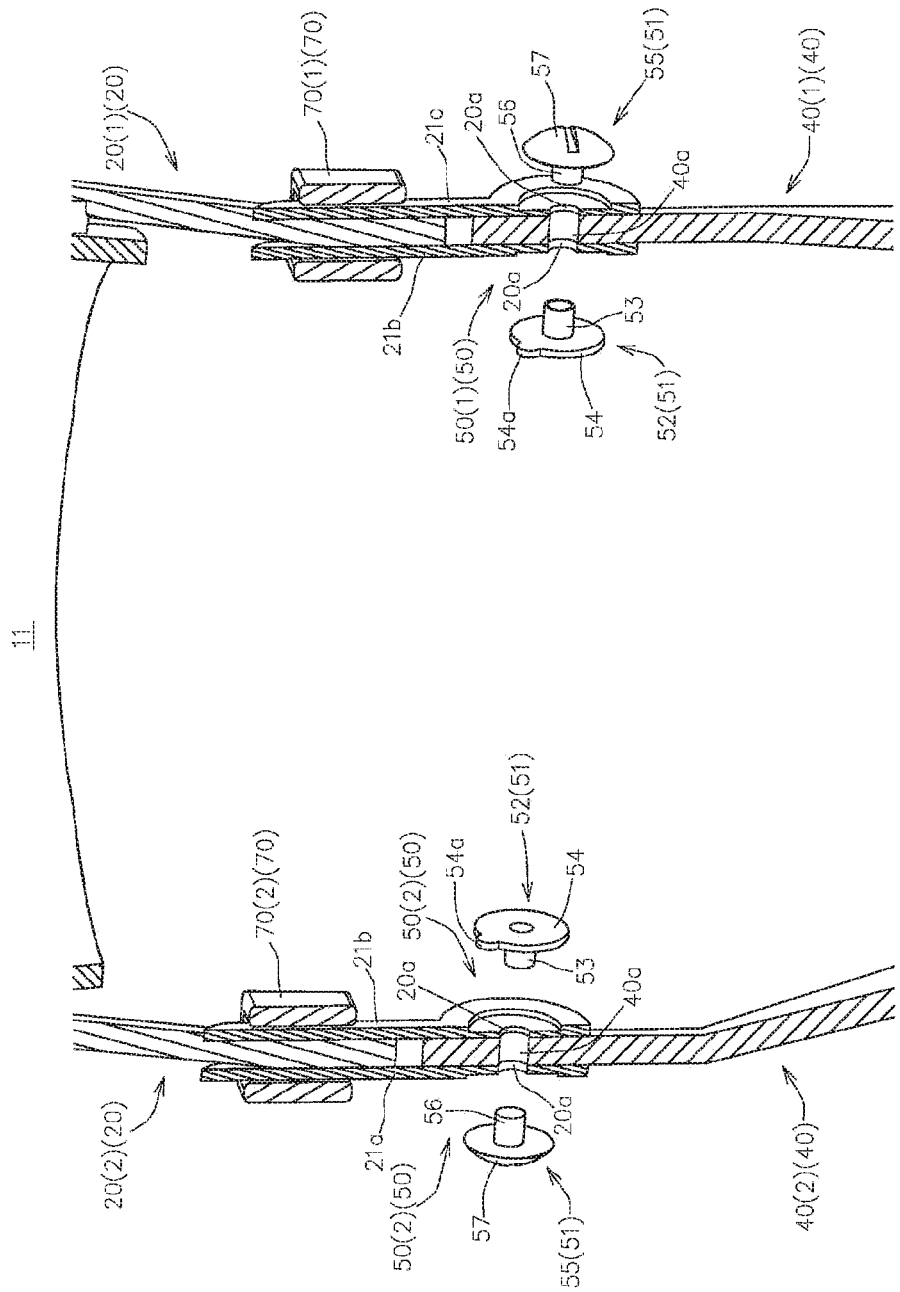
FIG. 7 is a vertical cross-sectional front view corresponding to FIG. 5.

FIG. 7 shows a vertical cross-sectional front view corresponding to FIG. 5.

In the present embodiment, as shown in FIGS. 5 to 7, the thigh frame 20 has a vertically extending thigh frame main body and a pair of connecting pieces 21a, 21b fixed to the respective sides in the user width direction of the lower end part of the frame main body by pinning, welding, or the like. The upper part of the lower leg frame 40 is interposed between the pair of connecting pieces 21a, 21b.

As shown in FIG. 6, the brace-side rotational connecting part 50 has a swinging connector 51 for connecting the thigh frame 20 and the lower leg frame 40 so as to be rotatable around the brace-side pivot axis line X by being inserted into a brace-side frame attachment hole formed by a thigh frame attachment hole 20a provided in the lower part of the thigh frame 20 coaxially with the brace-side pivot axis line X and a lower leg frame attachment hole 40a provided in the upper part of the lower leg frame 40 coaxially with the brace-side pivot axis line X.

In the present embodiment, as described above, the thigh frame 20 has a pair of connecting pieces 21a, 21b. Accordingly, the thigh frame attachment hole 20a is formed in each of the pair of connecting pieces 21a, 21b.

As shown in FIGS. 5 to 7, the swinging connector 51 has an internally threaded member 52 and an externally threaded member 55 separably screwed to each other in the brace-side frame attachment hole.

The internally threaded member 52 has a cylindrical part 53 to be inserted into the brace-side frame attachment hole from one side in the user width direction and a flange part 54 extending more radially outward than the brace-side frame attachment hole from one side in the user width direction of the cylindrical part 53. The cylindrical part 53 has a screw hole that is open toward the free end side.

On the other hand, the externally threaded member 55 has a cylindrical part 56 having an external thread to be screwed into the screw hole from the other side in the user width direction and a flange part 57 extending more radially outward than the brace-side frame attachment hole from the other side in the user width direction of the cylindrical part 56.

As shown in FIGS. 5 to 7, in the present embodiment, the internally threaded member 52 is inserted into the brace-side attachment hole from the inner side in the user width direction, and the externally threaded member 55 is screwed to the internally threaded member 52 from the outer side in the user width direction.

Reference number 54a in FIGS. 6 and 7 is a radially outward projection that is provided on the flange part 53 and that engages with a depression 22 (see FIG. 6) formed in the inner connecting piece 21b, and thereby the internally threaded member 52 is retained so as to be incapable of relative rotation around the axis line relative to the inner connecting piece 21b (i.e., the thigh frame 20).

In the present embodiment, as shown in FIGS. 5 to 7, the knee-ankle-foot orthosis 1 further has a locking member 70 for inhibiting the rotation of the lower leg frame 40 around the brace-side pivot axis line X relative to the thigh frame 20.

The locking member 70 is configured so as to be capable of reaching a locked state (the state shown in FIG. 5) where the thigh frame 20 and the lower leg frame 40 are surrounded by the locking member 70 to connect both frames 20, 40 and prevent the lower leg frame 40 from being relatively rotated around the brace-side pivot axis line X relative to the thigh frame 20, and a cancelled state where connection between the thigh frame 20 and the lower leg frame 40 is cancelled to permit the lower leg frame 40 to be relatively rotated around the brace-side pivot axis line X relative to the thigh frame 20.

In the present embodiment, the locking member 70 has a first locking member 70(1) positioned on the outer side in the user width direction and acting on the first thigh frame 20(1) and the first lower leg frame 40(1), and a second locking member 70(2) positioned on the inner side in the user width direction and acting on the second thigh frame 20(2) and the second lower leg frame 40(2).

In the present embodiment, as shown in FIG. 6, an upper-end surface 45 of the lower leg frame 40 (the end surface facing the thigh frame 20) is a sloped surface such that the radial distance from the brace-side pivot axis line X increases from one side toward the other side around the brace-side pivot axis line X, and a lower-end surface 25 of the thigh frame 20 (the end surface facing the lower leg frame 40) is a sloped surface corresponding to the upper-end surface 45 of the lower leg frame 40.

Due to this configuration, the lower leg frame 40 rotates only toward one side around the brace-side pivot axis line X relative to the thigh frame 20 (in the direction in which the user's lower leg is bent relative to the thigh) and does not rotate toward the other side (in the direction in which the user's lower leg is extended relative to the thigh).

Below, the actuator unit 100 on the gait motion assisting apparatus 1 according to the present embodiment will now be described.

As shown in FIGS. 1 to 3, the actuator unit 100 includes an upper frame 120 connectable to the thigh-side brace 10, a lower frame 140 connectable to the lower leg-side brace 30, an actuator-side rotational connecting part 150 connecting the upper frame 120 and the lower frame 140 such that the lower frame 140 is rotatable around an actuator-side pivot axis line Y relative to the upper frame 120, and a driver 110 for producing driving force for rotating the lower frame 140 around the actuator-side pivot axis line Y.

As shown in FIGS. 2 and 3, the upper frame 120 has a plate-like upper frame main body 121 facing the first thigh frame 20(1)(20), a connecting wall body 122 extending outward in the user width direction from the vertically intermediate position of the upper frame main body 121, and an outer wall body 123 extending downward from the connecting wall body 122.

In the present embodiment, the upper frame main body 121 is opposed to the first thigh frame 21(1) via inner cover main body 210.

That is, as shown in FIGS. 1 to 3, the actuator unit 100 has a cover 200 partially surrounding the upper frame 120, the driver 110, and the lower frame 140.

The cover 200 has an inner cover main body 210 fixed to the inner side in the user width direction of the upper frame main body 121, and an outer cover main body 220 detachably connected to the inner cover main body 210 so as to partially surround the upper frame 120 including the upper frame main body 121, the driver 110, and the lower frame 140.

In this configuration, the upper frame main body 121 is opposed to the first thigh frame 20(1) via the inner cover main body 210.

The outer wall body 123 is opposed to a downward extending portion 121a of the upper frame main body 121, which extends downward below the connecting wall body 122, while retaining an accommodating space in the user width direction between the outer wall body 123 and the downward extending portion 121a.

Figure 8:
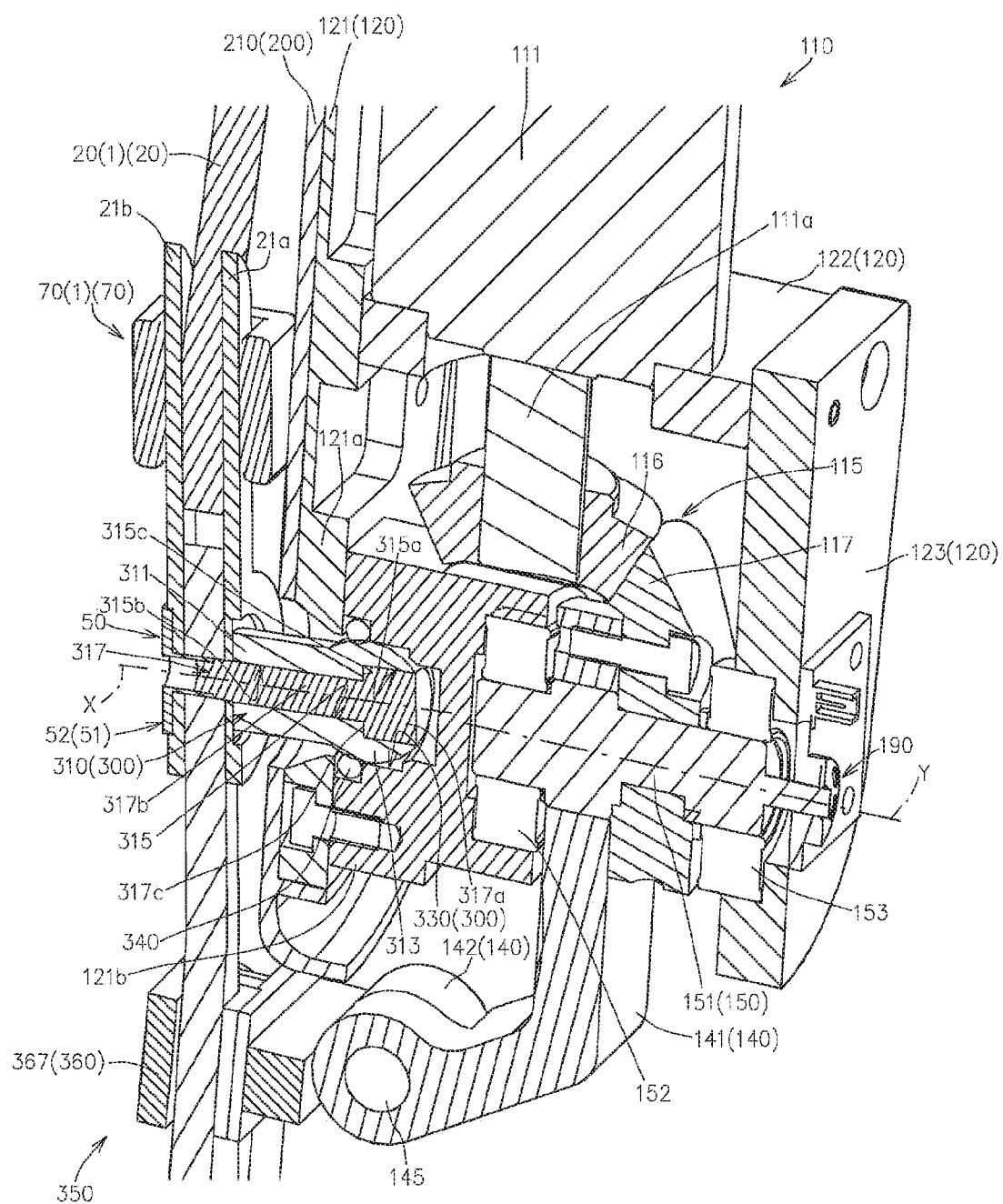
FIG. 8 is a partially enlarged vertical cross-sectional view of the vicinity of an intermediate connecting body in a state where the actuator unit is attached to the knee-ankle-foot orthosis.

FIG. 8 is a partially enlarged vertical cross-sectional view of a portion in the vicinity of the actuator-side rotational connecting part 150.

Figure 9:
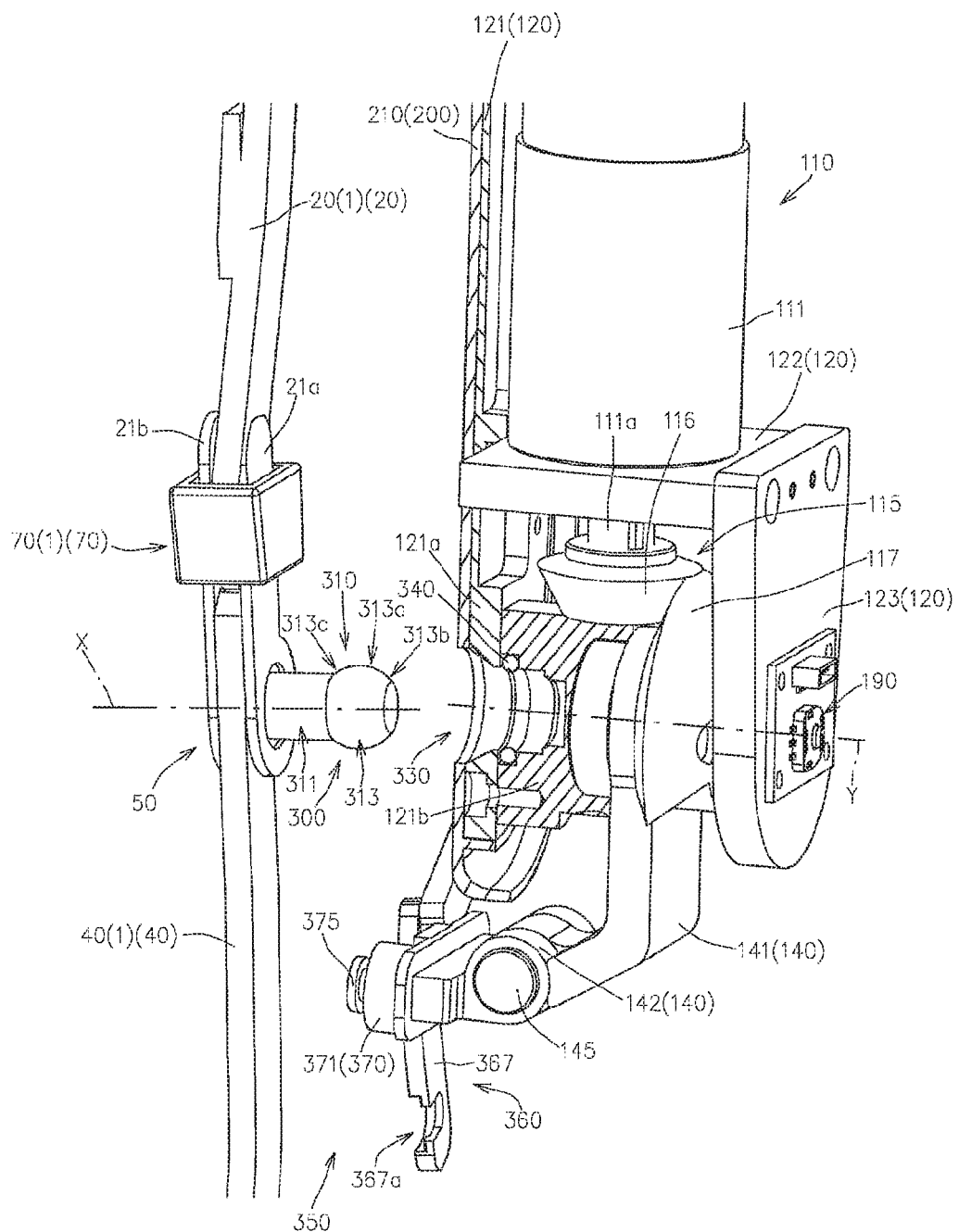
FIG. 9 is a partially exploded perspective view corresponding to FIG. 8, and shows cross-sections of only some components.

FIG. 9 is a partially exploded perspective view corresponding to FIG. 8, and shows cross-sections of only some components.

In FIGS. 8 and 9, illustration of the outer cover main body 220 is omitted.

The actuator-side rotational connecting part 150 connects the upper frame 120 and the lower frame 140 such that the lower frame 140 is rotatable around the actuator-side pivot axis line Y relative to the upper frame 120.

The actuator-side rotational connecting part 150 has a swing shaft 151 that supports the lower frame 140 and that is supported by the upper frame 120 so as to extend along the actuator-side pivot axis line Y.

In the present embodiment, as shown in FIGS. 8 and 9, the inner end part in the user width direction of the swing shaft 151 is supported by the downward extending portion 121a and the outer end part in the user width direction of the swing shaft 151 is supported by the outer wall body 123 such that the swing shaft 151 crosses the accommodating space in the user width direction and defines the actuator-side pivot axis line, and the intermediate part in the user width direction of the swing shaft 151 supports the lower frame 140.

In the present embodiment, the upper frame main body 121 has a block body 121b fixed to the outer side in the user width direction of the downward extending portion 121a, and the inner end side in the user width direction of the swing shaft 151 is supported so as to be axially rotatable by the block body 121b via a bearing member 152, and the outer side in the user width direction of the swing shaft 151 is supported so as to be axially rotatable by the outer wall body 123 via a bearing member 153.

The driver 110 has a driving source 111 such as an electric motor, and a transmission mechanism 115 for transmitting driving force produced by the driving source 111 to the lower frame 140.

The driving source 111 is supported by the upper frame 120.

In the present embodiment, as shown in FIGS. 2, 8, and 9, the driving source 111 is placed on the connecting wall body 122 of the upper frame 120, with an output shaft 111a extending downward.

In the present embodiment, as shown in FIG. 8, the transmission mechanism 115 has a drive-side bevel gear 116 supported by the output shaft 111a so as to be incapable of relative rotation, and a driven-side bevel gear 117 that is connected to the lower frame 140 so as to be incapable of relative rotation around the actuator-side pivot axis line Y and that is meshed with the drive-side bevel gear 116.

In the present embodiment, the lower frame 140 is supported by the swing shaft 151 so as to be incapable of relative rotation, and the actuator unit 100 includes a sensor 190 for detecting the angle of axial rotation of the swing shaft 151.

Detecting the angle of axial rotation of the swing shaft 151 by the sensor 190 enables the swinging angle of the lower frame 140 to be recognized.

The actuator unit 100 according to the present embodiment is detachably attached to three locations, i.e., the upper part, vertically intermediate part, and lower part, of the knee-ankle-foot orthosis 1.

Specifically, as shown in FIGS. 2, 3, 8, and 9, the actuator unit 100 has an upper connecting body 250 for connecting the upper frame 120 to the thigh frame 20, an intermediate connecting body 300 for connecting the vicinity of the actuator-side rotational connecting part 150 to the vicinity of the brace-side rotational connecting part 50, and a lower connecting body 350 for connecting the lower frame 140 to the lower leg frame 40 such that the lower leg frame 40 is rotated around the brace-side pivot axis line X relative to the thigh frame 20 by utilizing the rotational movement of the lower frame 140 around the actuator-side pivot axis line Y relative to the upper frame 120.

The intermediate connecting body 300 has a ball stud 310 provided on one of the knee-ankle-foot orthosis 1 and the actuator unit 100 (hereinafter referred to as a first unit), and an accommodation depression 330 that is provided on the other of the knee-ankle-foot orthosis 1 and the actuator unit 100 (hereinafter referred to as a second unit) and that receives the ball stud 310 by way of a ball-and-socket joint.

In the present embodiment, as shown in FIGS. 8 and 9, the knee-ankle-foot orthosis 1 is the first unit provided with the ball stud 310, and the actuator unit 100 is the second unit provided with the accommodation depression 330.

The ball stud 310 has a shaft part 311 that is provided concentrically with the pivot axis line (the brace-side pivot axis line X in the present embodiment) of the first unit in a projecting manner and that extends toward the second unit, and a spherical head part 313 provided at the distal end part of the shaft part 311.

As described above, in the present embodiment, the knee-ankle-foot orthosis 1 is the first unit, and the knee-ankle-foot orthosis is the second unit. Accordingly, the shaft part 311 is provided on the knee-ankle-foot orthosis 1 in a projecting manner so as to extend toward the actuator unit 100 coaxially with the brace-side pivot axis line X.

In the present embodiment, the ball stud 310 is provided on the knee-ankle-foot orthosis 1 in a projecting manner by utilizing the swinging connector 51.

Specifically, as shown in FIG. 8, the ball stud 310 is provided on the knee-ankle-foot orthosis 1 in a projecting manner by being screw-connected to the inner threaded member positioned on the inner side in the user width direction among the internally threaded member 52 and the externally threaded member 55 (the internally threaded member 52 in the present embodiment) in place of the outer threaded member positioned on the outer side in the user width direction among the internally threaded member 52 and the externally threaded member 55 (the externally threaded member 55 in the present embodiment) in the swinging connector 51.

Specifically, as shown in FIG. 8, the ball stud 310 has an axial hole 315 penetrating in the axial direction, and the ball stud 310 is screw-connected to the inner threaded member via a fastening member 317 such as a bolt inserted in the axial hole 315.

Specifically, the axial hole 315 has a large diameter hole 315a that is open on the side where the spherical head part 313 is positioned with respect to the axial direction, a small diameter hole 315b that is open on the side opposite to the spherical head part 313 with respect to the axial direction, and a step 315c connecting the large diameter hole 315a and the small diameter hole 315b.

The fastening member 317 has a head part 317a inserted in the large diameter hole 315a and a shaft part 317b that is reduced in diameter from the head part 317a via a radially extending part 317c and that penetrates the small diameter hole 315b to extend outward.

The radially extending part 317c can be brought into contact with the step 315c. A portion of the shaft part 317b extending outward, with the radially extending part 317c being in contact with the step 315c, has a screw structure screwed to the inner threaded member.

According to this configuration, the ball stud 310 can be easily provided on the existing knee-ankle-foot orthosis 1 in a projecting manner so as to be coaxial with the brace-side pivot axis line X.

The actuator unit 100 according to the present embodiment has the following configuration for preventing the ball stud 310 from being unintentionally dislocated from the accommodation depression 330.

Specifically, as shown in FIG. 9, the spherical head part 313 has a large diameter part 313a having the largest diameter, a distal end-side spherical surface part 313b, the diameter of which is reduced toward the distal end side from the large diameter part 313a, and a proximal end-side spherical surface part 313c, the diameter of which is reduced toward the proximal end side from the large diameter part 313a.

The accommodation depression 330 is provided with an annular engagement groove at a portion, which the proximal end-side spherical surface part 313c of the spherical head part 313 faces when the spherical head part 313 is accommodated in the accommodation depression 330, and a retaining member 340 is inserted into the annular engagement groove.

The retaining member 340 is shaped such that force for expanding the retaining member 340 in the radially outward direction is exerted on the retaining member by the movement of the spherical head part 313 in the axial direction, and the retaining member 340 is inserted into the annular engagement groove so as to prevent passage of the maximum diameter part 313a of the spherical head part 313 when the force resulting from the axial movement of the spherical head part 313 is equal to or less than a predetermined value and so as to be elastically deformed in the radially outward direction by the spherical head part 313 and permit passage of the maximum diameter part 313a of the spherical head part 313 when the force exceeds the predetermined value.

The retaining member 340 is formed by, for example, inserting an elongated body having a circular cross-section in a spirally wound state into the annular engagement groove and retaining it in a circular shape, and thereby the retaining member 340 is elastically deformable in the radially outward direction while being inserted in the annular engagement groove.

According to the intermediate connecting body 300 having this configuration, by moving the actuator unit 100 inward in the user width direction relative to the knee-ankle-foot orthosis 1 such that the ball stud 310 is accommodated in the accommodation depression 330, the vicinity of the actuator-side rotational connecting part 150 of the actuator unit 100 can remain connected to the vicinity of the brace-side rotational connecting part 50 of the knee-ankle-foot orthosis 1 without precisely matching the brace-side pivot axis line X and the actuator-side pivot axis line Y, and by moving the actuator unit 100 outward in the user width direction from the knee-ankle-foot orthosis 1 (by moving the actuator unit 100 outward in the user width direction by force exceeding the predetermined value when the retaining structure is provided), connection between the vicinity of the actuator-side rotational connecting part 150 and the vicinity of the brace-side rotational connecting part 50 can be cancelled.

Figure 10:
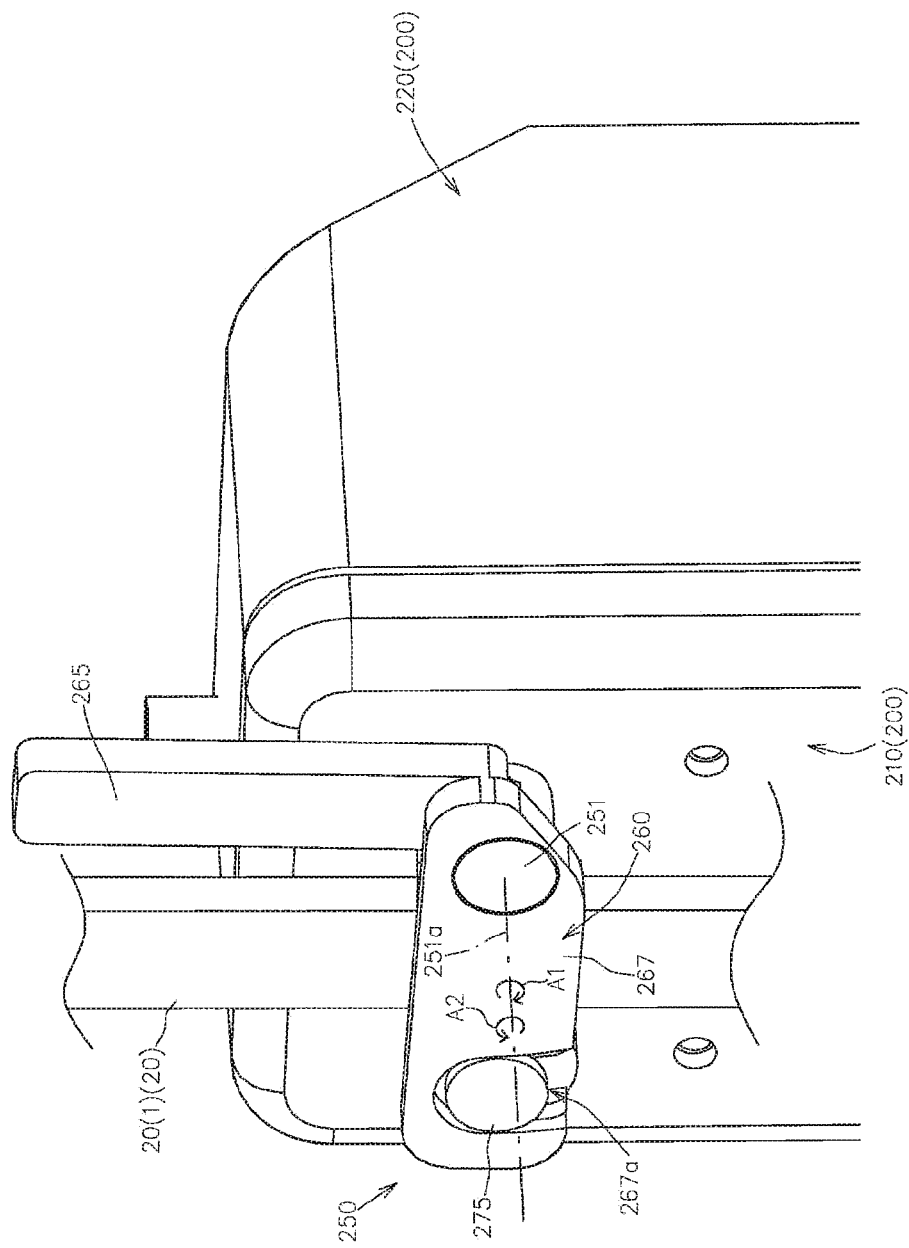
FIG. 10 is a perspective view of the vicinity of an upper connecting part as viewed from the inner side in the user width direction in a state where the actuator unit is attached to the knee-ankle-foot orthosis.

FIG. 10 is a perspective view of the vicinity of the upper connecting part 250 as viewed from the inner side in the user width direction.

In FIG. 10, illustration of the thigh attachment 10 is omitted for easier understanding.

As shown in FIG. 10, the upper connecting body 250 includes an upper rotational shaft 251 provided on the upper frame 120 so as to extend inward in the user width direction (in the state of penetrating the inner cover main body 210 in the present embodiment) and an upper fastening member 260 supported by the upper rotational shaft 251 so as to be rotatable around an axis line 251a.

Figure 11:
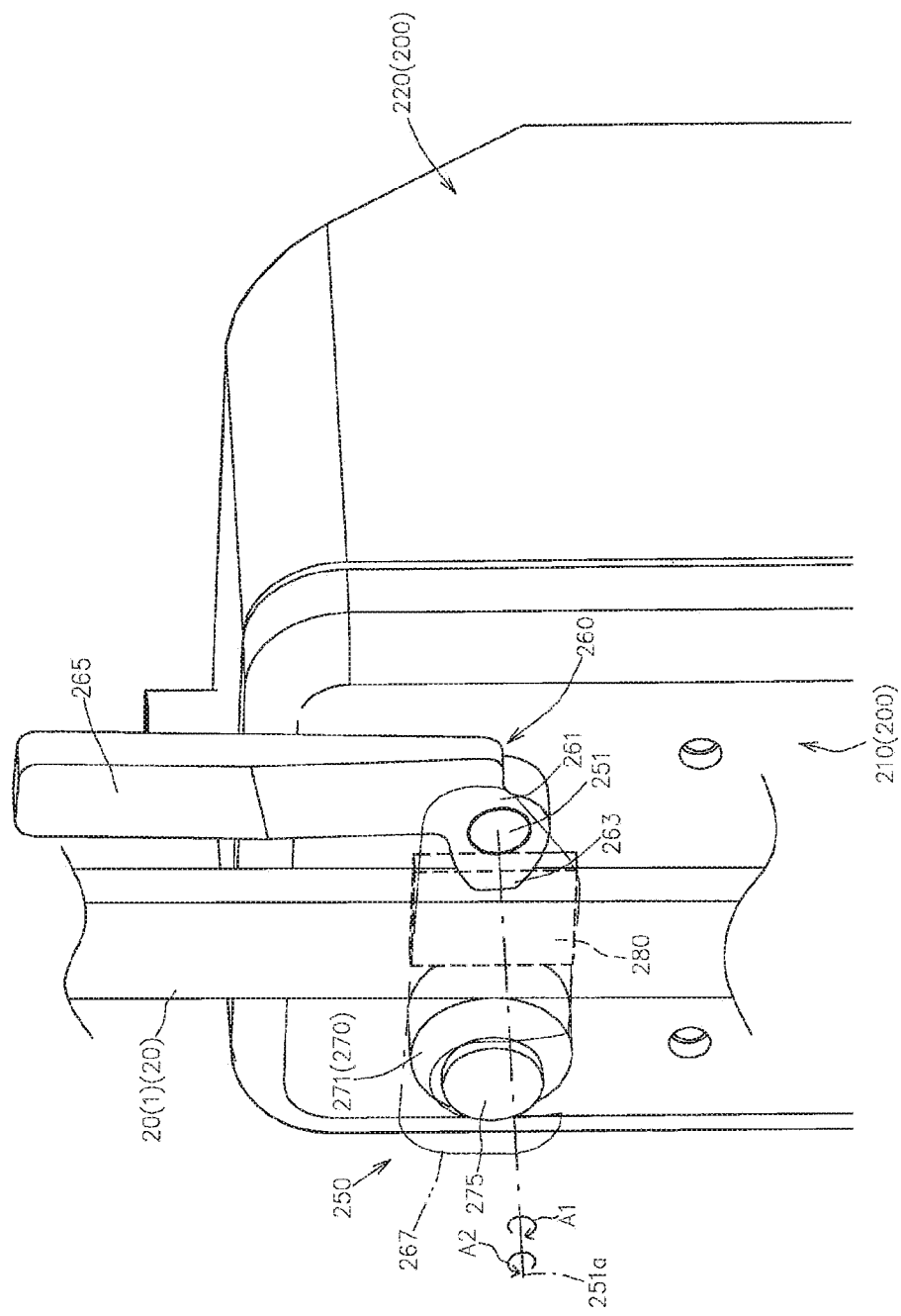
FIG. 11 is a cross-sectional perspective view corresponding to FIG. 10, and shows a state where an upper fastening member is positioned in a held position.

FIG. 11 is a partial cross-sectional perspective view in which a part of the upper fastening member 260 in the state depicted in FIG. 10 is cut away.

As shown in FIG. 11, the upper fastening member 260 has a bearing part 261 supported by the upper rotational shaft 251 and a cam part 263 extending radially outward from the bearing part 261.

The cam part 263 is configured such that the radial distance between the outer circumferential surface and the axis line 251a of the upper rotational shaft 251 is increased toward a first side A1 around the axis line 251a of the upper rotational shaft 251.

As shown in FIG. 11, the upper connecting body 250 further includes an upper receiving member 270 supported (in the state of penetrating the inner cover main body 210 in the present embodiment) by the upper frame 20 in a position spaced apart in the user front-back direction from the upper rotational shaft 251 only a distance that enables the thigh frame 20 to be interposed between the upper receiving member 270 and the upper rotational shaft 251.

In the present embodiment, the upper connecting body 250 includes the upper receiving shaft 275 provided (in the state of penetrating the inner cover main body 210 in the present embodiment) on the upper frame 120 so as to extend inward in the user width direction, and an elastic roller 271 supported by the upper receiving shaft 275 acts as the upper receiving member 270.

Figure 12:
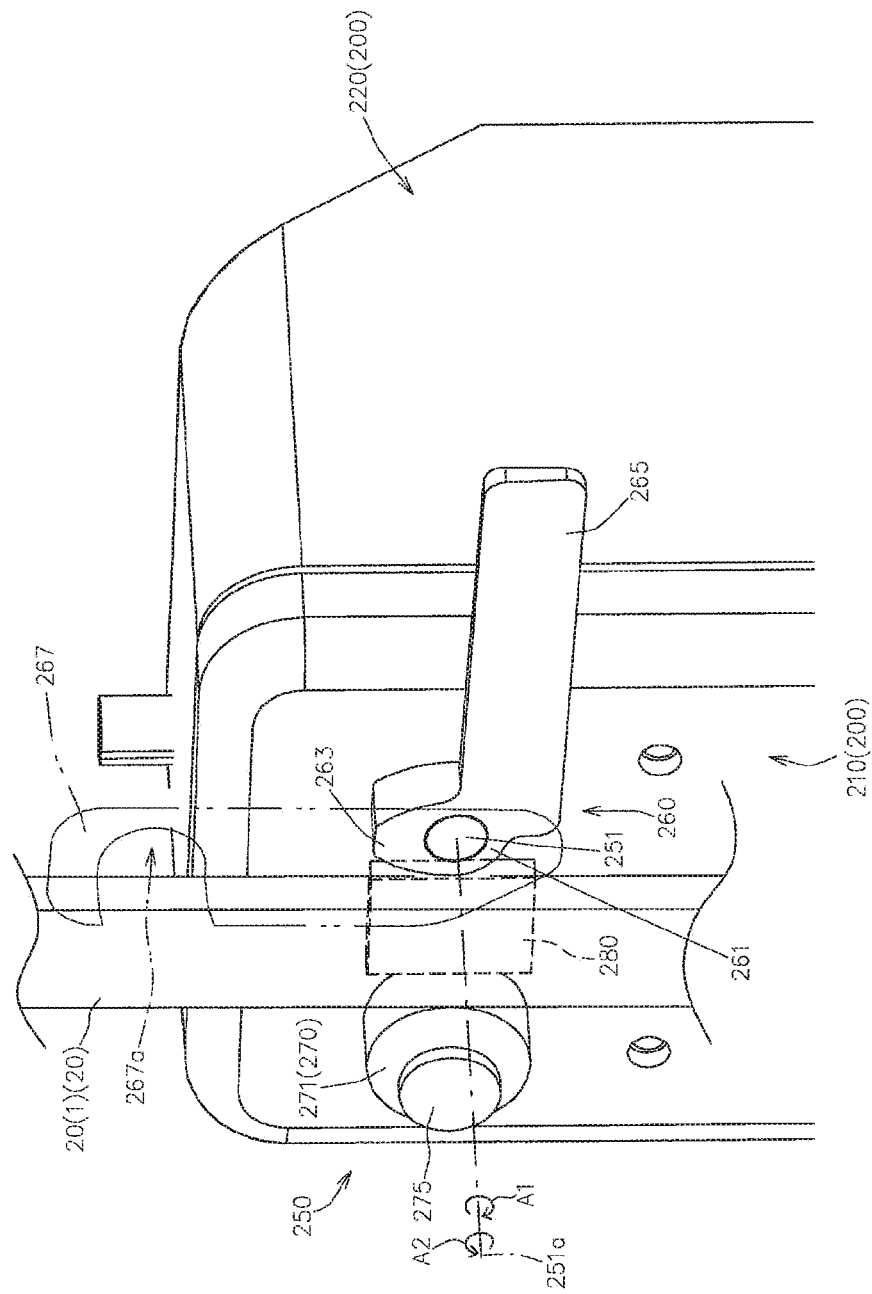
FIG. 12 is a cross-sectional perspective view corresponding to FIG. 10, and shows a state where the upper fastening member is positioned in a released position.

FIG. 12 is a partial cross-sectional perspective view corresponding to FIG. 11, and shows the state where the upper fastening member 260 is positioned in a predetermined released position around the upper rotational shaft 251.

As shown in FIG. 12, in the state where the upper fastening member 260 is positioned in a released position around the upper rotational shaft 251, relatively moving the upper frame 120 and the thigh frame 20 toward each other with respect to the user width direction enables the thigh frame 20 to be positioned in the space between the upper fastening member 260 and the upper receiving member 270, and in the state where the thigh frame 20 is positioned in the space, relatively moving the upper frame 120 and the thigh frame 20 away from each other with respect to the user width direction enables the thigh frame 20 to be retreated from the space.

Moreover, as shown in FIG. 11, in the state where the thigh frame 20 is positioned in the space, rotating the upper fastening member 260 from the released position around the upper rotational shaft 251 to a second side A2 opposite to the first side A1 around the axis line causes the cam part 263 to hold the thigh frame 20 in cooperation with the upper receiving member 270 with respect to the user front-back direction, and thereby the state where the upper frame 120 is connected to the thigh frame 20 is attained.

As shown in FIGS. 10 to 12, in the present embodiment, the upper fastening member 260 has an operation arm 265 extending radially outward from the bearing part 261 in a position circumferentially different from the cam part 263.

The operation arm 265 is configured such that the radial length between the free end of the operation arm 265 and the axis line 251a of the upper rotational shaft 251 is greater than the radial length between the radially outermost end of the cam part 263 and the axis line 251a of the upper rotational shaft 251.

This configuration, while making it easy to rotate the upper fastening member 260 around the upper rotational shaft 251 via the operation arm 265, makes it possible to effectively prevent connection between the upper frame 120 and the thigh frame 20 from being cancelled by the rotation of the upper fastening member 260 around the upper rotational shaft 251 via the cam part 263 when the thigh frame 20 and the upper frame 120 are relatively moved unintentionally.

As shown in FIGS. 10 to 12, in the present embodiment, the upper fastening member 260 has an engagement arm 267 extending radially outward from the bearing part 261 on the inner side in the user width direction than the cam part 263.

In FIGS. 11 and 12, the engagement arm 267 is indicated by an imaginary line (dashed double-dotted line).

The engagement arm 267 is provided on the upper fastening member 260 so as to be positioned on the inner side in the user width direction than the thigh frame 20 positioned in the space between the upper fastening member 260 and the upper receiving member 270.

The engagement arm 267 is provided with an engagement groove 267a for engagement with a portion of the upper receiving shaft 275, which extends more inward in the user width direction than the upper receiving member 270, when the upper fastening member 260 is rotated around the upper rotational shaft 251 from the released position toward the second side A2 around the axis line to hold the thigh frame 20 with respect to the user front-back direction in cooperation with the upper receiving member 270, and by the inward extending portion of the upper receiving shaft 275 inserted in the engagement groove 267a, the unintentional relative movement of the upper frame 120 and the thigh frame 20 in the user width direction is prevented.

Reference number 280 in FIGS. 11 and 12 denotes a spacer for filling the gap between the thigh frame 20 and the upper frame 120 (the inner case main body 210 in the present embodiment) with respect to the user width direction when the thigh frame 20 is positioned in the space between the upper fastening member 260 and the upper receiving member 270 and the upper fastening member 260 is positioned in a held position. The spacer is preferably a rubber body.

Next, the lower connecting body 350 will be now described.

Figure 13:
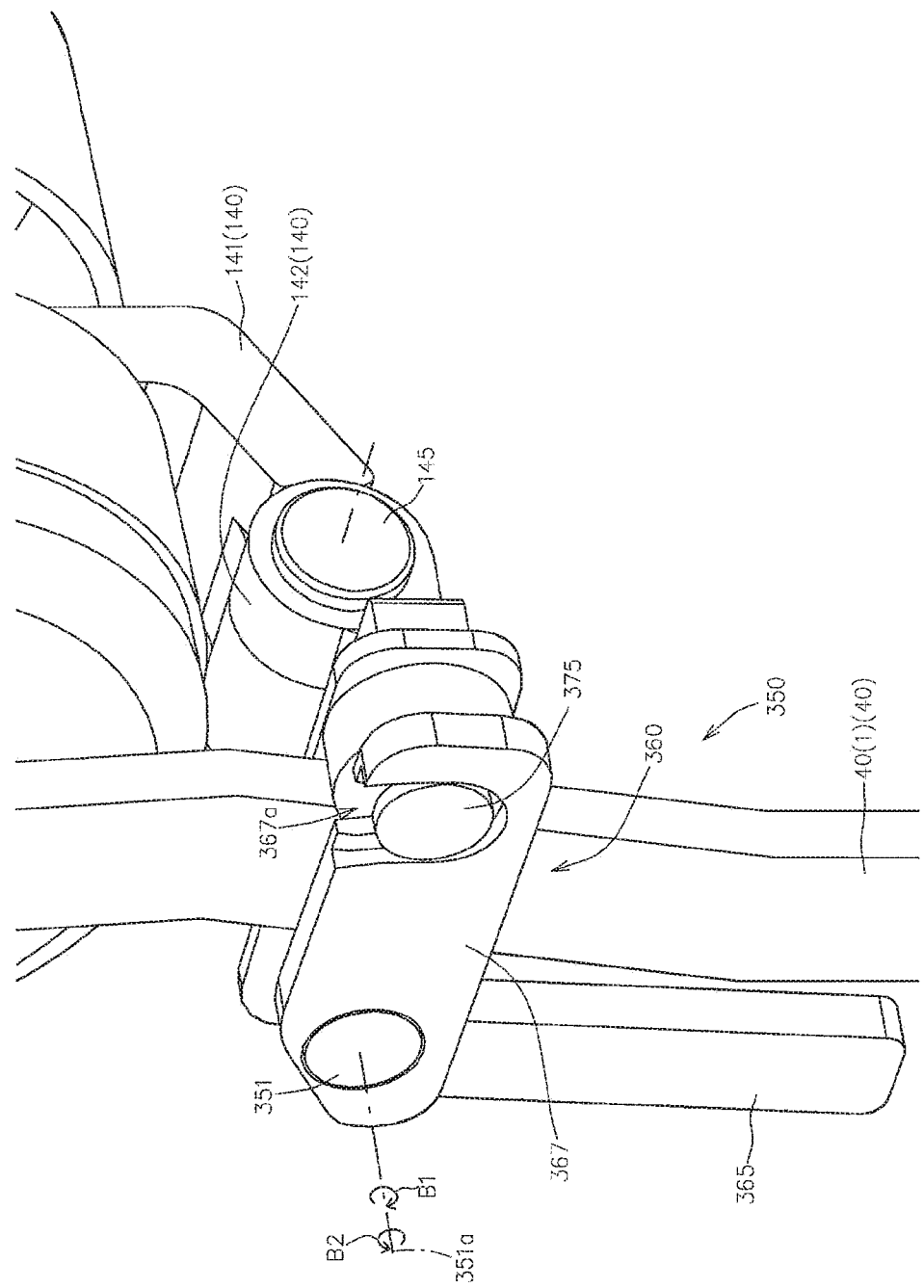
FIG. 13 is a partial perspective view of the vicinity of a lower connecting body as viewed from the inner side in the user width direction in a state where the actuator unit is attached to the knee-ankle-foot orthosis.

FIG. 13 shows a perspective view of the vicinity of the lower connecting body 350 as viewed from the inner side in the user width direction.

In FIG. 13, illustration of the lower leg attachment 30 is omitted for easier understanding.

As shown in FIG. 13, the lower connecting body 350 includes a lower rotational shaft 351 provided on the lower frame 140 so as to extend inward in the user width direction and a lower fastening member 360 supported by the lower rotational shaft 351 so as to be rotatable around an axis line 351a.

Figure 14:
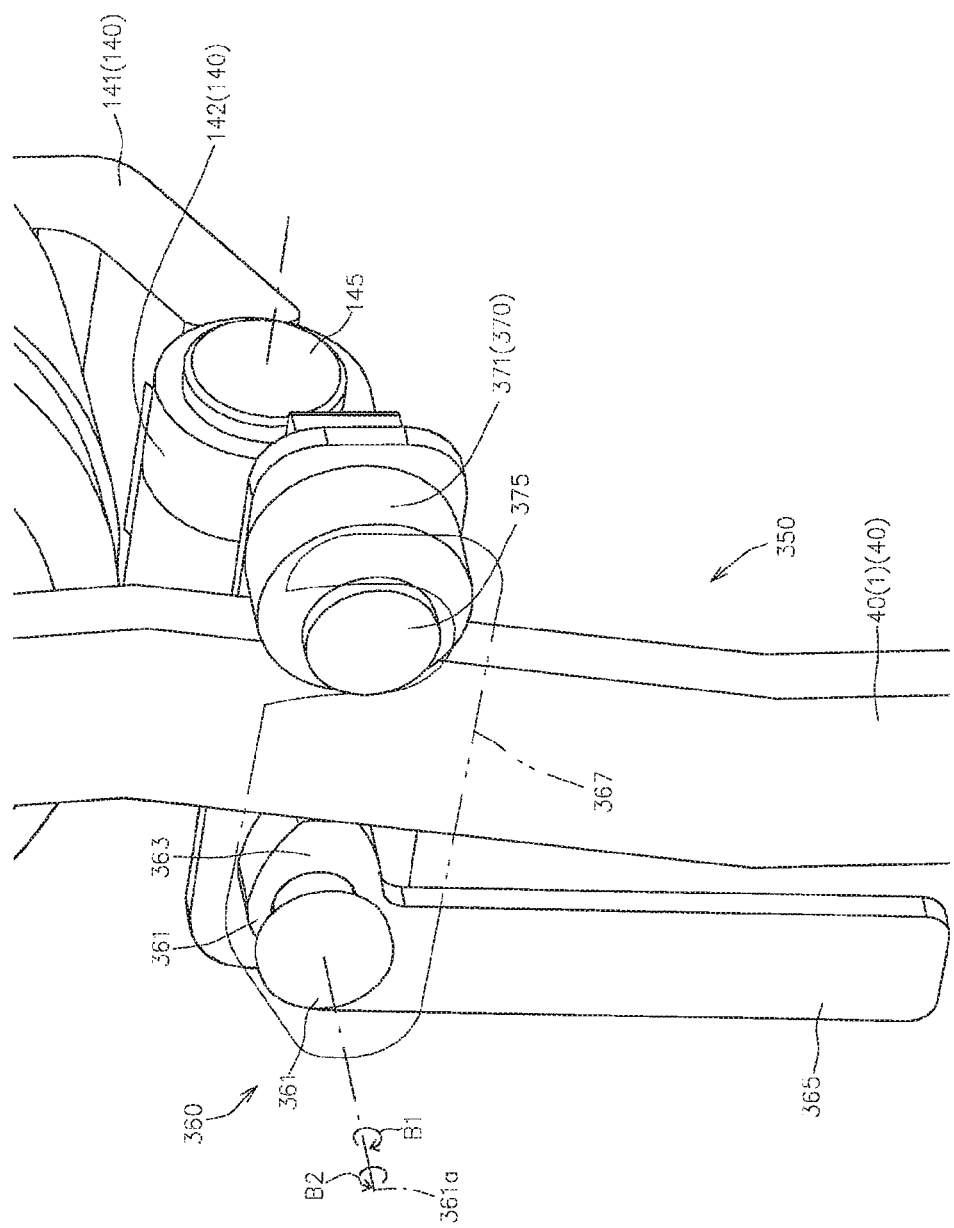
FIG. 14 is a cross-sectional perspective view corresponding to FIG. 13, and shows a state where a lower fastening member is positioned in a held position.

FIG. 14 is a partial cross-sectional perspective view in which a part of the lower fastening member 360 in the state depicted in FIG. 13 is cut away.

As shown in FIG. 14, the lower fastening member 360 has a bearing part 361 supported by the lower rotational shaft 351 and a cam part 363 extending radially outward from the bearing part 361.

The cam part 363 is configured such that the radial distance between the outer circumferential surface and the axis line 351a of the lower rotational shaft 351 is increased toward a first side B1 around the axis line 351a of the lower rotational shaft 351.

As shown in FIG. 14, the lower connecting body 350 further includes a lower receiving member 370 supported by the lower frame 140 in a position spaced apart in the user front-back direction from the lower rotational shaft 351 only a distance that enables the lower leg frame 40 to be interposed between the lower fastening member 360 and the lower rotational shaft 351.

In the present embodiment, the lower connecting body 350 includes a lower receiving shaft 375 provided on the lower frame 140 so as to extend inward in the user width direction, and an elastic roller 371 supported by the lower receiving shaft 375 acts as the lower receiving member 370.

FIG. 15 is a partial cross-sectional perspective view corresponding to FIG. 14, and shows the state where the lower fastening member 360 is positioned in a predetermined released position around the lower rotational shaft 351.

As shown in FIG. 15, in the state where the lower fastening member 360 is positioned in a released position around the lower rotational shaft 351, relatively moving the lower frame 140 and the lower leg frame 40 toward each other with respect to the user width direction enables the lower leg frame 40 to be positioned in the space between the lower fastening member 360 and the lower receiving member 370, and in the state where the lower leg frame 40 is positioned in the space, relatively moving the lower frame 140 and the lower leg frame 40 away from each other with respect to the user width direction enables the lower leg frame 40 to be retreated from the space.

Moreover, as shown in FIG. 14, in the state where the lower leg frame 40 is positioned in the space, axially rotating the lower fastening member 360 from the released position around the lower rotational shaft 351 to a second side B2 opposite to the first side B1 causes the cam part 363 to hold the lower leg frame 40 in cooperation with the lower receiving member 370 with respect to the user front-back direction, and thereby the state where the lower frame 140 is connected to the lower leg frame 40 is attained.

As shown in FIGS. 13 to 15, in the present embodiment, the lower fastening member 360 has an operation arm 365 extending radially outward from the bearing part 361 in a position circumferentially different from the cam part 363.

The operation arm 365 is configured such that the radial length between the free end of the operation arm 365 and the axis line 351a of the lower rotational shaft 351 is greater than the radial length between the radially outermost end of the cam part 363 and the axis line 351a of the lower rotational shaft 351.

This configuration, while making it easy to rotate the lower fastening member 360 around the lower rotational shaft 351 via the operation arm 365, makes it possible to effectively prevent connection between the lower frame 140 and the lower leg frame 40 from being cancelled by the rotation of the lower fastening member 360 around the lower rotational shaft 351 via the cam part 363 when the lower leg frame 40 and the lower frame 140 are relatively moved unintentionally.

As shown in FIGS. 13 to 15, in the present embodiment, the lower fastening member 360 has an engagement arm 367 extending radially outward from the bearing part 361 in a position more inside in the user width direction than the cam part 363.

In FIG. 14 and FIG. 15, the engagement arm 367 is indicated by an imaginary line (dashed double-dotted line).

The engagement arm 367 is provided on the lower fastening member 360 so as to be positioned on the inner side in the user width direction than the lower leg frame 40 positioned in the space between the lower fastening member 360 and the lower receiving member 370.

The engagement arm 367 is provided with an engagement groove 367a for engagement with a portion of the lower receiving shaft 375, which extends more inward in the user width direction than the lower receiving member 370, when the lower fastening member 360 is rotated around the lower rotational shaft 351 from the released position toward the second side B2 around the axis line to hold the lower leg frame 40 with respect to the user front-back direction in cooperation with the lower receiving member 370, and by the inward extending portion of the lower receiving shaft 375 inserted in the engagement groove 367a, the unintentional relative movement of the lower frame 140 and the lower leg frame 40 in the user width direction is prevented.

The lower connecting body 350 is also provided with a spacer 380 (see FIG. 3) for filling the gap between the lower leg frame 40 and the lower frame 140 with respect to the user width direction when the lower fastening member 360 is positioned in a held position, with the lower leg frame 40 being positioned in the space between the lower fastening member 360 and the lower receiving member 370.

Moreover, with the actuator unit 100 in the present embodiment being attached to the knee-ankle-foot orthosis 1, the position in the user width direction of the lower connecting body 350 is adjustable, and, accordingly, the actuator unit 100 can be effectively attached to knee-ankle-foot orthoses having various shapes and sizes.

That is, as shown in, for example, FIGS. 8, 9, and 13 to 15, the lower frame 140 includes a first lower frame 141 connected to the upper frame 120 via the actuator-side rotational connecting part 150 so as to be rotatable around the actuator-side pivot axis line Y, and a second lower frame 142 directly or indirectly supporting the lower rotational shaft 351 and the lower receiving member 370, and the second lower frame 142 is connected to the first lower frame 141 so as to be rotatable around a swing shaft 145 in the user front-back direction.

This configuration makes it possible to change the orientation of the attached actuator unit 100, and thus the actuator unit 100 can be appropriately attached to variously shaped knee-ankle-foot orthoses 1 that are custom-made according to the user's physique.

That is, the knee-ankle-foot orthosis 1 is custom-made according to the user's physique, and thus the tilt angle and/or the curvature of the thigh frame 20 relative to the lower leg frame 40 with respect to the user width direction W (see FIG. 4) is different for each knee-ankle-foot orthosis 1.

In this regard, adopting the configuration in which the second lower frame 142 directly or indirectly supporting the lower rotational shaft 351 and the lower receiving member 370 is connected so as to be rotatable around the swing shaft 145 in the user front-back direction to the first lower frame 141 connected to the upper frame 120 via the actuator-side rotational connecting part 150 so as to be rotatable around the actuator-side pivot axis line Y enables the actuator unit 100 to be effectively attached to various knee-ankle-foot orthoses 1 having different tilt angles and/or curvatures with respect to the user width direction W of the thigh frame 20 relative to the lower leg frame 40.

Here, the control structure of the actuator unit 100 will now be described.

The actuator unit 100 recognizes a gait state during gait cycle based on a thigh phase angle, and performs operational control for the driver 110 such that gait assisting force suitable for the gait state is imparted.

As described above, the actuator unit 100 imparts gait assisting force to the lower leg.

That is, the actuator unit 100 is configured to detect movement of not the lower leg that is a control target site but the thigh that is a site different from the lower leg, and impart gait assisting force to the lower leg that is a control target site based on movement of the thigh.

Figure 16:
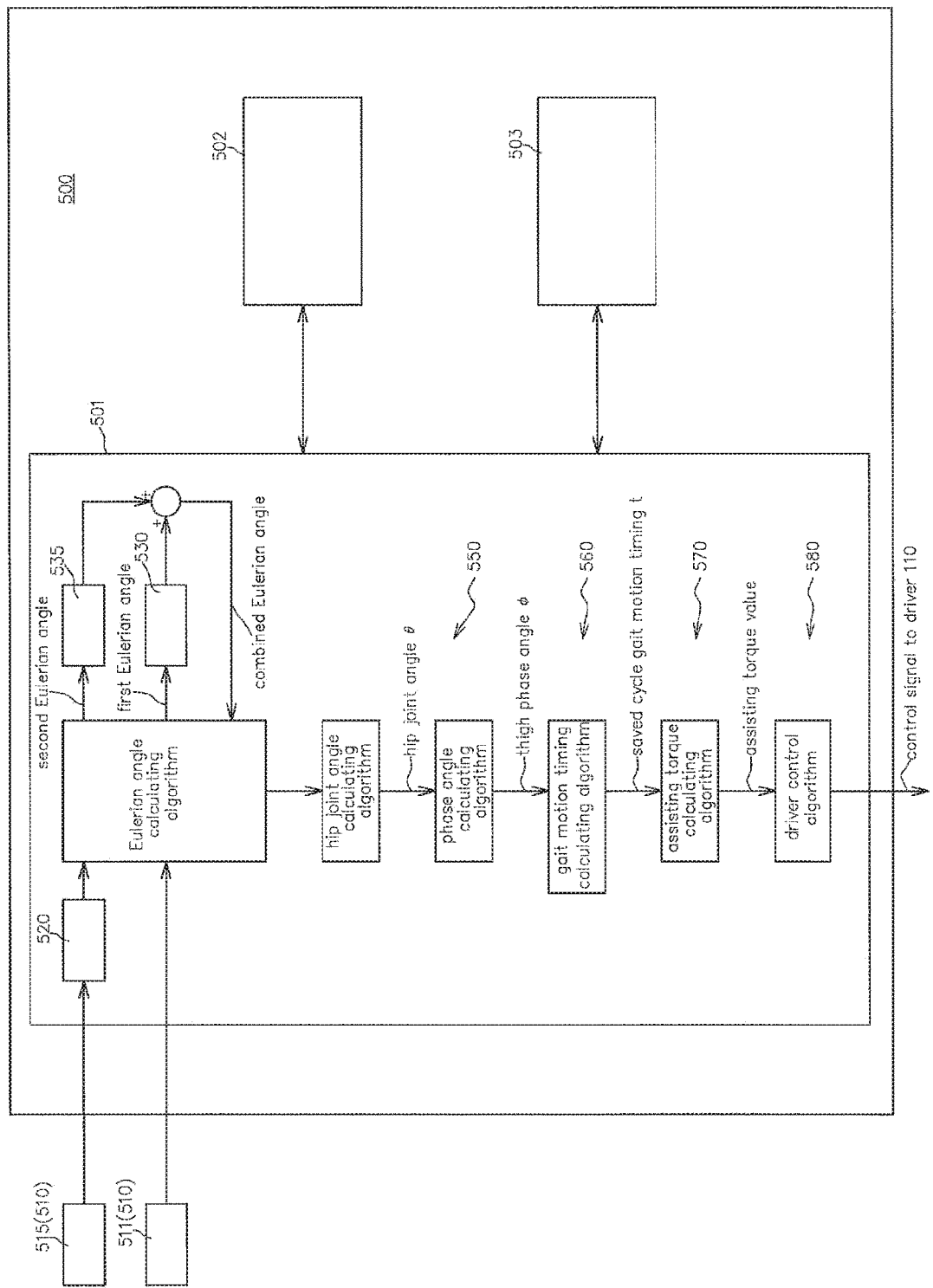
FIG. 16 is a control block diagram of the actuator unit.

FIG. 16 shows a control block diagram of the actuator unit 100.

Specifically, the actuator unit 100 includes a thigh orientation detecting means 510 capable of detecting an angle-related signal relating to a hip joint angle that is a front-back swing angle of a user's thigh; a thigh phase angle calculating means 550 for calculating a thigh phase angle based on the angle-related signal; a gait motion timing calculating means 560 for converting the thigh phase angle into a gait state (a gait motion timing) during gait cycle; an assisting torque calculating means 570 for calculating a torque value that should be output at the gait motion timing; and a driver control means 580 responsible for operational control for the driver 110.

As shown in FIG. 1, the actuator unit includes an actuator-side control device 500.

As shown in FIG. 16, in the present embodiment, the actuator-side control device 500 acts as the thigh phase angle calculating means 550, the gait motion timing calculating means 560, the assisting torque calculating means 570, and the driver control means 580.

Specifically, as shown in FIG. 16, the actuator-side control device 500 has an actuator-side control part 501 including a control processing means for executing processing based on a signal received from the thigh orientation detecting means 510, a manually operated member, or the like; an actuator-side storage part 502 including a ROM storing a control program, control data, and the like, a non-volatile storage means storing a setting value or the like such that the setting value or the like is not lost even when a power supply is interrupted and is rewritable, a RAM temporarily storing data generated during processing by the processing part, or the like; and an actuator-side wireless communication part 503 for performing wireless communication such as Bluetooth® communication with the terminal device 600.

The thigh orientation detecting means 510 detects the angle-related signal at each predetermined specific sampling timing during gait cycle.

The thigh orientation detecting means 510 may have various forms such as a gyro sensor, an acceleration sensor, and a rotary encoder as long as it can directly or indirectly detect the front-back swing angle of the thigh (the hip joint angle).

For example, the thigh orientation detecting means 510 can be configured to have only an acceleration sensor, and in this case, the thigh phase angle during walking can be calculated from the acceleration (or position) and speed of the acceleration sensor without calculating the hip joint angle.

In the present embodiment, the thigh orientation detecting means 510 has a triaxial angular velocity sensor (a gyro sensor) 511 capable of detecting the front-back swing angle velocity of the thigh, and is configured such that the thigh phase angle calculating means 550 calculates the hip joint angle, which is the front-back swing angle of the thigh, by integrating the angular velocity of the thigh detected by the triaxial angular velocity sensor 511.

In the gait motion assisting apparatus according to the present embodiment, as shown in FIG. 16, the actuator unit 100 includes a triaxial acceleration sensor 515, and the thigh phase angle calculating means 550 is configured to calculate the hip joint angle (the front-back swing angle of the thigh) in which the vertical axis line that the triaxial acceleration sensor 515 detects when the user is in a standstill is the reference value.

Instead, the actuator unit 100 can be configured not to have the triaxial acceleration sensor 515.

In this case, the hip joint angle (the front-back swing angle of the thigh) calculated by the thigh phase angle calculating means 550 is the thigh front-back swing angle in which an angle that the thigh phase angle calculating means 550 calculates when the main power source of the gait motion assisting apparatus 1 is turned on is the reference value.

Thus, in this case, the thigh phase angle calculating means 550 can correct the hip joint angle (the front-back swing angle of the thigh) by using a high-pass filter so that the median value of the hip joint angle is the reference value thereof.

Alternatively, instead of using a high pass filter, the thigh phase angle calculating means 550 can detect a deviation between the maximum value in the positive direction and the maximum value in the negative direction of a calculated hip joint angle (front-back swing angle of the thigh) and, based on the deviation, correct calculated hip joint angle so that the median value of the hip joint angle is the reference values thereof.

While it is also possible to detect the front-back swing angle of the thigh relative to the body axis line by a rotary encoder and use the detected value as a hip joint angle, in the present embodiment, the hip joint angle is calculated based on an angular velocity detected by the triaxial angular velocity sensor 511, and thereby the degree of design freedom of the gait motion assisting apparatus is increased.

That is, in a case where the hip joint angle (the thigh front-back swing angle relative to the body axis line) is detected by a rotary encoder, it is necessary to detect the angle of relative movement between a torso-side detector secured to the torso and a thigh-side detector secured to the thigh so as to swing integrally with the thigh, and it is therefore necessary to attach both detectors such that the torso-side detector and the thigh-side detector do not positionally shift relative to the torso and the thigh, respectively.

On the other hand, the method of calculating a hip joint angle based on an angular velocity detected by the triaxial angular velocity sensor 511 does not have the above-described restrictions and can provide enhanced design freedom of the gait motion assisting apparatus.

As described above, in the actuator unit 100 in the gait motion assisting apparatus according to the present embodiment, the thigh orientation detecting means 510 has a triaxial acceleration sensor 515 in addition to the triaxial angular velocity sensor 511.

In this case, the thigh phase angle calculating means 550 is configured to calculate a combined Eulerian angle by combining a high-frequency component of a first Eulerian angle calculated based on angular velocity data from the triaxial angular velocity sensor 511 and a low-frequency component of a second Eulerian angle calculated based on acceleration data from the triaxial acceleration sensor 515, and calculate a thigh phase angle based on a hip joint angle calculated from the combined Eulerian angle and a hip joint angular velocity calculated from the hip joint angle.

Specifically, as shown in FIG. 16, the thigh phase angle calculating means 550 receives sensor coordinate axis-based angular velocity data from the triaxial angular velocity sensor 511 at every sampling timing, and converts the angular velocity data into angular velocity data (Eulerian angular velocity) that indicates a correlation between a sensor coordinate axis and a global coordinate axis (a vertical direction-based spatial coordinate axis) using a predetermined conversion formula.

Then, the thigh phase angle calculating means 550 integrates the angular velocity data (Eulerian angular velocity) to calculate the first Eulerian angle.

Preferably, the thigh phase angle calculating means 550 can perform drift elimination on sensor coordinate axis-based angular velocity data received from the triaxial angular velocity sensor 511 at every predetermined sampling timing using angular velocity data received from the triaxial angular velocity sensor 511 when the user is in standstill (or when the user is not in motion).

Moreover, the thigh phase angle calculating means 550 receives sensor axis-based acceleration data from the triaxial acceleration sensor 515 at every sampling timing via a low-pass filter 520, and calculates the second Eulerian angle indicating a correlation between a sensor coordinate axis and a global coordinate axis (a vertical direction-based spatial coordinate axis) from the acceleration data received via the low-pass filter 520, based on acceleration data received when the user is in standstill (or when the user is not in motion) and gravitational acceleration.

Then, the thigh phase angle calculating means 550 calculates a hip joint angle θ from a unit vector indicating the orientation of the thigh and the combined Eulerian angle obtained by combining the high-frequency component of the first Eulerian angle obtained via a high-pass filter 530 and the low-frequency component of the second Eulerian angle obtained via the low-pass filter 535.

Preferably, the thigh phase angle calculating means 550 can perform drift elimination by detecting heel contact based on acceleration data from the acceleration sensor 515 and, when heel contact is detected, adding a corrected Eulerian angle calculated from angular velocity data from the triaxial angular velocity sensor 511 to the combined Eulerian angle.

A thigh phase angle $\varphi$ is calculated by the following algorithm.

The thigh phase angle calculating means 550, at every sampling timing, calculates a hip joint angle $\theta$ and, also, differentiates it to calculate a hip joint angular velocity $\omega$.

For example, the thigh phase angle calculating means 550 calculates a hip joint angle $\theta k$ at the $k^{th}$ sampling timing Sk (k is an integer of 1 or greater) from a gait cycle reference timing, and then differentiates it to calculate a hip joint angular velocity $\omega k$ at the sampling timing Sk.

Then, the thigh phase angle calculating means 550 calculates a thigh phase angle $\varphi k$ (=−Arctan($\omega k/\theta k$)) at the sampling timing Sk based on the hip joint angle $\theta k$ and the hip joint angular velocity $\omega k$ at the sampling timing Sk.

In the actuator unit 100, the thigh phase angle calculating means 550 is configured to plot, when a hip joint angle $\theta$ and a hip joint angular velocity $\omega$ are calculated based on an angle-related signal, a thigh motion state defined by the hip joint angle $\theta$ and the hip joint angular velocity $\omega$ on a phase angle plane to create a trajectory diagram.

Figure 17:
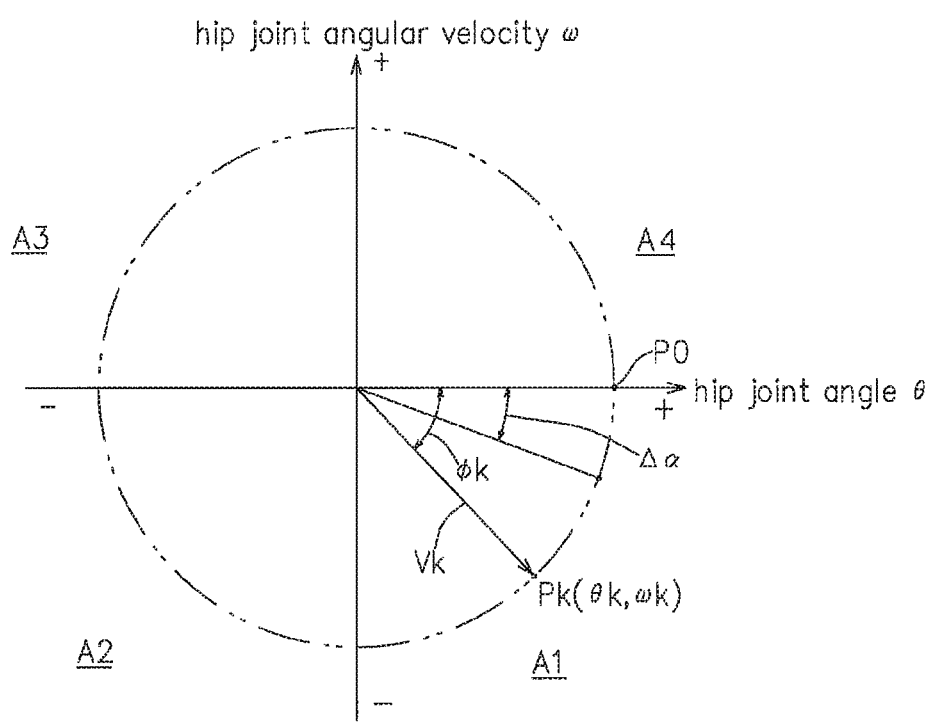
FIG. 17 is a trajectory diagram obtained by plotting a hip joint angle θ and a hip joint angular velocity ω over a gait cycle, which are calculated by an actuator-side control device in the actuator unit.

FIG. 17 shows a trajectory diagram obtained by plotting thigh motion states (gait states) defined by the hip joint angle $\theta$ and the hip joint angular velocity $\omega$ over a gait cycle.

As shown in FIG. 17, the thigh phase angle $\varphi$ determined by the hip joint angle $\theta$ and the hip joint angular velocity $\omega$ varies between 0 and 2n in a gait cycle.

Specifically, the hip joint angle in a state where the thigh is positioned in front of and behind the vertical axis line is referred to as "positive" and "negative", respectively, and the hip joint angular velocity in a state where the thigh is swung forward and backward is referred to as "positive" and "negative", respectively.

Under this condition, if the phase angle in a state where the hip joint angle is largest in the "positive" direction and the hip joint angular velocity is "zero" (point P0 in FIG. 17) is regarded as 0, a gait area A1 in FIG. 17 (a gait area from a state where the hip joint angle $\theta$ is largest in the "positive" direction and the hip joint angular velocity $\omega$ is "zero" to a state where the hip joint angle $\theta$ is "zero" and the hip joint angular velocity $\omega$ is largest in the "negative" direction) corresponds to the phase angle of 0 to $\pi/2$.

Also, a gait area A2 in FIG. 17 (a gait area from a state where the hip joint angle $\theta$ is "zero" and the hip joint angular velocity is largest in the "negative" direction to a state where the hip joint angle is largest in the "negative" direction and the hip joint angular velocity is "zero") corresponds to the phase angle of $\pi/2$ to $\pi$.

Moreover, a gait area A3 in FIG. 17 (a gait area from a state where the hip joint angle $\theta$ is largest in the "negative" direction and the hip joint angular velocity $\omega$ is "zero" to a state where the hip joint angle $\theta$ is "zero" and the hip joint angular velocity $\omega$ is largest in the "positive" direction) corresponds to the phase angle of n to $3\pi/2$.

Also, a gait area A4 in FIG. 17 (a gait area from a state where the hip joint angle $\theta$ is "zero" and the hip joint angular velocity is largest in the "positive" direction to a state where the hip joint angle is largest in the "positive" direction and the hip joint angular velocity is "zero") corresponds to the phase angle of $3\pi/2$ to $2\pi$.

The sampling timing of the thigh orientation detecting means 510 is determined such that a plurality of sampling timings are included in a gait cycle, and the thigh phase angle calculating means 550 calculates the thigh phase angle $\varphi$ at each sampling timing.

In the present embodiment, the thigh phase angle calculating means 550 determines whether the vector length of a plot point Pk (the distance between the origin of the trajectory diagram (i.e., the point where the hip joint angle $\theta$ and the hip joint angular velocity $\omega$ are zero) and the plot point Pk) defined by the hip joint angle $\theta k$ and the hip joint angular velocity $\omega k$ on the trajectory diagram exceeds a predetermined threshold value and, when the vector length exceeds the predetermined threshold value, calculates a thigh phase angle $\varphi k$ that is based on the hip joint angle $\theta k$ and the hip joint angular velocity $\omega k$, and sends the thigh phase angle $\varphi k$ to the gait motion timing calculating means 560.

On the other hand, when the vector length is less than or equal to the predetermined threshold value, the thigh phase angle calculating means 550 outputs an actuator operation inhibitory signal.

This configuration enables the actuator unit 100 to be effectively prevented from being operated when gait motion is not started.

That is, a user wearing the actuator unit 100 may unintentionally change posture over a small range before starting gait motion. In particular, in the case of a user with hemiplegia or the like, such a situation likely arises.

When the thigh phase angle calculating means 550 has the above configuration, such a minor posture change is detected as a vector having a short vector length.

Accordingly, by determining that gait motion is being performed only when the vector length of the vector Vk (see FIG. 17) defined by the hip joint angle $\theta k$ and the hip joint angular velocity $\omega k$ exceeds a predetermined threshold value, the actuator unit 100 can be effectively prevented from being unintentionally operated when gait motion is not started.

The gait motion timing calculating means 560 has a phase pattern function that defines a relationship between a thigh phase angle $\varphi$ and a gait motion timing during gait cycle, and applies the thigh phase angle $\varphi$ at a sampling timing sent from the thigh phase angle calculating means 550 to the phase pattern function to calculate which gait motion timing during gait cycle said the sampling timing corresponds to (which timing the sampling timing of the thigh phase angle $\varphi$ corresponds to, when a gait cycle is 100%).

Moreover, the gait motion timing calculating means 560, every time a gait cycle is completed, calculates the latest phase pattern function by performing the least-squares method on effective phase angle data including past phase angle data stored at that time and the latest phase angle data in which the thigh phase angle $\varphi$ in the completed gait cycle and the gait motion timing corresponding to the thigh phase angle $\varphi$ are associated with each other, and overwrite-saves the calculated latest phase pattern function.

Figure 18:
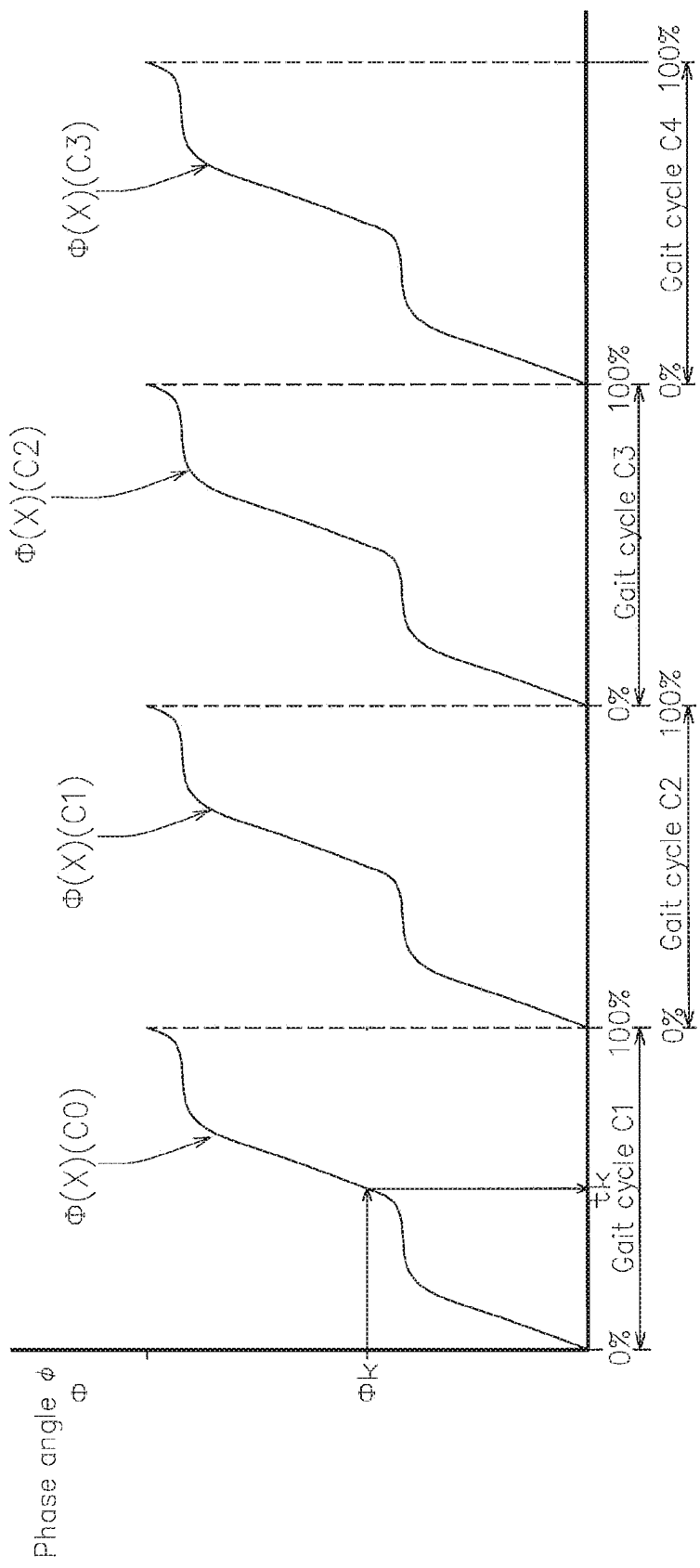
FIG. 18 is a graph of a phase pattern function showing a relationship between a thigh phase angle and a gait motion timing during gait cycle.

Specifically, as shown in FIG. 18, an initial phase pattern function $\varphi(x)(C0)$ is stored as the phase pattern function in the gait motion timing calculating means 560 in an initial state.

This initial phase pattern function $\varphi(x)(C0)$ is created for each user and stored in the gait motion timing calculating means 560 in advance.

For example, during a first gait cycle C1, the thigh phase angle calculating means 550 calculates $\varphi k$ as a thigh phase angle at a sampling timing Sk and sends it to the gait motion timing calculating means 560.

At this time, the first gait cycle C1 is not yet completed, and thus the gait motion timing calculating means 560 has the initial phase pattern function φ(x)(C0) as the phase pattern function.

Accordingly, the gait motion timing calculating means 560, as shown in FIG. 18, applies the thigh phase angle φk sent from the thigh phase angle calculating means 550 to the initial phase pattern function φ(x)(C0) to calculate a saved cycle gait motion timing tk corresponding to the sampling timing Sk, and sends it to the assisting torque calculating means 570.

The gait motion timing calculating means 560 repeats this processing until the first gait cycle C1 is completed.

Completion of a gait cycle can be determined, for example, based on whether the thigh phase angle φ defined by the hip joint angle θ and the hip joint angular velocity ω has returned to a preset gait cycle reference angle.

The gait motion timing calculating means 560, when the first gait cycle C1 is completed, adds the latest phase angle data in which a thigh phase angle received from the thigh phase angle calculating means 550 during the completed first gait cycle C1 and a gait motion timing corresponding to the thigh phase angle are associated with each other to past phase angle data stored at that time (in this example, phase angle data created by the initial phase pattern function φ(x)(C0)), creates effective phase angle data that is effective at that time, calculates the latest phase angle pattern function (in this example, a phase pattern function upon first gait cycle completion φ(x)(C1)) by performing the least-squares method on the effective phase angle data, and overwrite-saves the latest phase angle pattern function.

Specifically, when the first gait cycle C1 is completed, the gait motion timing calculating means 560 performs the least-squares method on the effective phase angle data that is effective at that time to calculate the coefficient parameter of:

$$\varphi(x)(C1)=a_0(1)+a_1(1)x+a_2(1)x^2+ \ldots +a_m(1)x^m$$

and save φ(x)(C1) as a phase pattern function of the thigh phase angle. In the above formula, m is a positive integer.

Then, in the second gait cycle C2, the gait motion timing calculating means 560 uses the phase pattern function upon first gait cycle completion φ(x)(C1) stored at that time to calculate a saved cycle gait motion timing tk.

When the second gait cycle C2 is completed, the gait motion timing calculating means 560 performs the least-squares method on the effective phase angle data that is effective at that time to calculate the coefficient parameter of:

$$\varphi(x)(C2)=a_0(2)x+a_1(2)x+a_2(2)x^2+ \ldots +a_m(2)x^m$$

and overwrite-save φ(x)(C2) as a phase pattern function of the thigh phase angle.

Then, in the third gait cycle C3, the gait motion timing calculating means 560 uses the phase pattern function upon second gait cycle completion φ(x)(C2) stored at that time to calculate a saved cycle gait motion timing.

The gait motion timing calculating means 560 repeats this processing.

The effective phase angle data may include the phase angle data of all gait cycles that have been completed by that time and, alternatively, depending on the storage capacity of the gait motion timing calculating means 560, may be limited to only the phase angle data of the latest gait cycles (such as 100 gait cycles).

In the present embodiment, having the following configuration, the gait motion timing calculating means 560 prevents abnormal phase angle data from being included in the effective phase angle data at the time of calculating a phase angle pattern function.

That is, the gait motion timing calculating means 560 calculates a difference ΔT between a current cycle gait motion timing Tk calculated based on a thigh phase angle φk at a sampling timing Sk received from the thigh phase angle calculating means 550 and a saved cycle gait motion timing tk calculated by applying the thigh phase angle φk to the phase pattern function φ(x) stored at that time.

Here, the current cycle gait motion timing Tk is calculated by:

$$Tk=(\varphi k/2\pi)\times 100(\%)$$

When the absolute value of the difference ΔT is less than or equal to a predetermined threshold value, the gait motion timing calculating means 560 stores the current cycle gait motion timing Tk as effective phase angle data to be used when calculating a new phase pattern function φ(x) upon completion of a gait cycle.

That is, when the absolute value of the difference ΔT is less than or equal to a predetermined threshold value, the gait motion timing calculating means 560 when calculating the latest phase pattern function upon completion of a gait cycle stores the current cycle gait motion timing Tk as a gait motion timing to be associated with a thigh phase angle φ received from the thigh phase angle calculating means 550 in the gait cycle.

On the other hand, when the absolute value of the difference ΔT exceeds a predetermined threshold value, the gait motion timing calculating means 560 stores the saved cycle gait motion timing tk as effective phase angle data to be used when calculating the latest phase pattern function upon completion of a gait cycle.

That is, when the absolute value of the difference ΔT exceeds a predetermined threshold value, the gait motion timing calculating means 560 when calculating the latest phase pattern function upon completion of a gait cycle stores the saved cycle gait motion timing tk as a gait motion timing to be associated with a thigh phase angle φ received from the thigh phase angle calculating means 550 in the gait cycle.

This configuration enables a current cycle gait motion timing Tk that has become an abnormal value for some reason to be effectively prevented from being included in the target data (effective phase angle data) at the time of calculating a phase pattern function.

The assisting torque calculating means 570 applies a gait motion timing tk sent from the gait motion timing calculating means 560 to output pattern saved data that is saved in the actuator-side control device 500 and that defines a relationship between a gait motion timing during gait cycle and a torque value to be output, to calculate a torque value that should be output at the sampling timing Sk.

The actuator-side control device 500 stores output pattern setting data sent from the terminal device 600 as the output pattern saved data.

This point will be described below.

The driver control means 580 executes operational control for the driver such that assisting force having a torque value calculated by the assisting torque calculating means 570 is output.

Thus, the actuator unit 100 is configured such that a gait state (a gait motion timing) during gait cycle is calculated based on a thigh phase angle φ, and assisting force corresponding to the gait state is output.

Accordingly, assisting force suitable for a gait state during gait cycle can be output.

Also, the actuator unit 100 is configured to apply the thigh phase angle $\varphi$ at a sampling timing to the phase pattern function stored at that time to calculate a gait state (a gait motion timing) at the sampling timing.

Accordingly, even when irregular gait motion is performed during a gait cycle, corrected assisting force can be output.

In the actuator unit 100, the thigh phase angle calculating means 550, only when the vector length of a plot point on a trajectory diagram defined by the hip joint angle $\theta$ and the hip joint angular velocity $\omega$ exceeds a predetermined threshold value, calculates a thigh phase angle $\varphi$ that is based on the hip joint angle $\theta$ and the hip joint angular velocity $\omega$ and sends the thigh phase angle $\varphi$ to the gait motion timing calculating means and, on the other hand, when the vector length is less than or equal to the predetermined threshold, outputs an actuator operation inhibitory signal.

Accordingly, in the case where a user wearing the actuator unit 100 unintentionally changes posture, the actuator unit 100 can be effectively prevented from outputting gait assisting force even when gait motion is not started.

Moreover, the actuator unit 100, as described above, is configured to recognize a gait state (a gait motion timing) during gait cycle based on the thigh phase angle $\varphi$ and then impart gait assisting force to the lower leg by the driver 110.

Accordingly, suitable gait assisting force can be supplied also to a user with hemiplegia due to a stroke or the like.

That is, conventional gait assisting devices configured to impart gait assisting force by a driver such as an electric motor are configured to detect movement of a control target site itself to which assisting force is to be imparted by the driver, and perform operational control for the driver based on the detection result.

For example, in conventional gait assisting devices that supply gait assisting force to the thigh, operational control for a driver that imparts gait assisting force to the thigh is performed based on the result of detecting thigh movement.

Also, in conventional gait assisting devices that supply gait assisting force to the lower leg, operational control for a driver that imparts gait assisting force to the lower leg is performed based on the result of detecting lower leg movement.

However, in the case of a patient with hemiplegia due to a stroke or the like, gait motion of the lower leg (forward and backward swing motion around the knee joint) often cannot be performed normally, while gait motion of the thigh (forward and backward swing motion around the hip joint) can be performed relatively normally.

When attempting to impart gait assisting force to the lower leg of such a patient, in the above conventional gait assisting devices, operational control for a driver that provides gait assisting force to the lower leg is performed based on the movement of the lower leg that is incapable of normal gait motion and, possibly, suitable gait assisting force cannot be provided.

On the other hand, the actuator unit 100 of the gait motion assisting apparatus according to the present embodiment is configured to perform operational control for the driver 110 that imparts gait assisting force to the lower leg based on the thigh phase angle $\varphi$ as described above.

Accordingly, even in the case of a user with hemiplegia due to a stroke or the like, suitable gait assisting force can be supplied to the lower leg.

Next, the terminal device 600 will now be described.

The terminal device 600 has a display part, an input part, a terminal-side control part, a terminal-side storage part, and a terminal-side wireless communication part for performing wireless communication with the actuator-side control device.

For example, the terminal device 600 may take various forms such as a personal computer including a keyboard and/or a mouse acting as the input part and a liquid crystal display acting as the display part, a personal computer including the display part having a touch panel function in place of, or in addition to, the keyboard and/or the mouse, moreover a tablet terminal having a touch panel acting as the display part and the input part, and a smart phone.

In the present embodiment, the terminal device 600 is a tablet terminal in consideration of operational convenience.

That is, as shown in FIG. 1, the terminal device 600 has a touch panel 610 acting as the display part and the input part, a terminal-side control part 601, a terminal-side storage part 602, and a terminal-side wireless communication part 603 for performing wireless communication such as Bluetooth® communication with the actuator-side wireless communication part 503.

Figure 19:
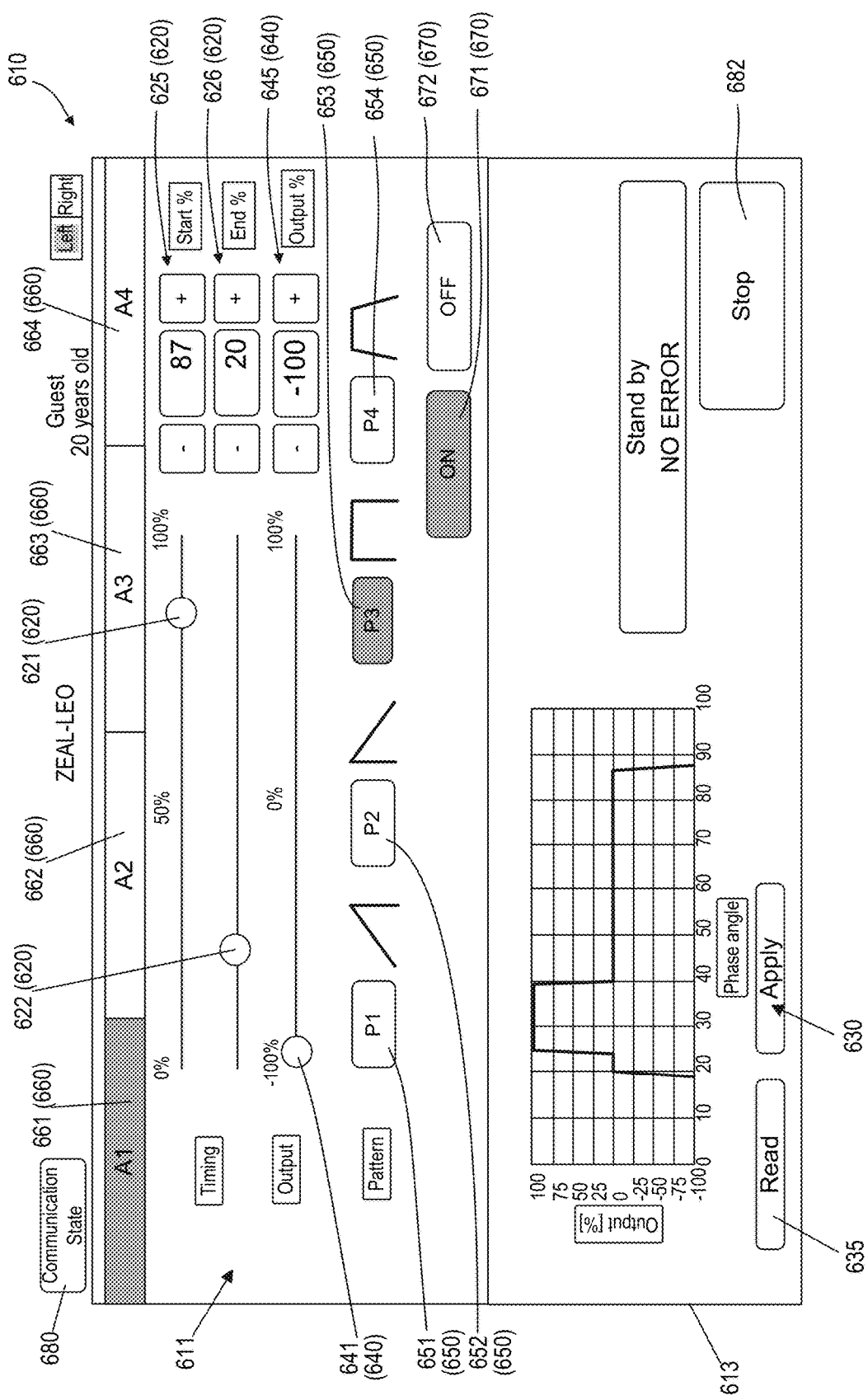
FIG. 19 is a front view of a touch panel of a tablet in the gait motion assisting apparatus.

FIG. 19 shows a front view of the touch panel 610.

The touch panel 610 includes a display part such as LCD or organic EL, and an input part superimposed on the display part and capable of detecting touch operation of an operator by a coordinate detection mechanism.

Various methods may be employed in the coordinate detection mechanism, such as a resistance film method in which a voltage produced when two pieces of film are brought into contact with each other by manual operation (such as touch operation, flick operation, and swipe operation) on the input part is detected, and a capacitance method in which a change in capacitance resulting from manual operation on the input part is detected.

The touch panel 610 is capable of receiving an assisting force setting value including an assisting force imparting period obtained by specifying a period for imparting assisting force to the lower frame 140 during gait cycle by using a gait motion timing during gait cycle.

Specifically, the display part is configured to display timing setting keys 620.

Through the timing setting keys 620, it is possible to input, for example, as the assisting force imparting period, a gait motion timing for starting assisting force application (an assisting force start timing) and a gait motion timing for ending assisting force application (an assisting force end timing) specified by using percentage relative to a gait cycle under a condition where a preset reference gait motion timing during gait cycle is regarded as a zero point.

In the present embodiment, as shown in FIG. 19, the display part displays, as the timing setting keys 620, an assisting force start timing slider key 621 and an assisting force end timing slider key 622 for inputting an assisting force start timing and an assisting force end timing, respectively.

The slider keys 621, 622 can be slidably operated between the "0" position corresponding to the reference gait motion timing and the "100" position corresponding to the timing at which a gait cycle having, as a starting point, the reference gait motion timing ends.

The reference gait motion timing is any gait state (any gait motion timing) during gait cycle, and is stored in the actuator-side control part 601 in advance.

Figure 20:
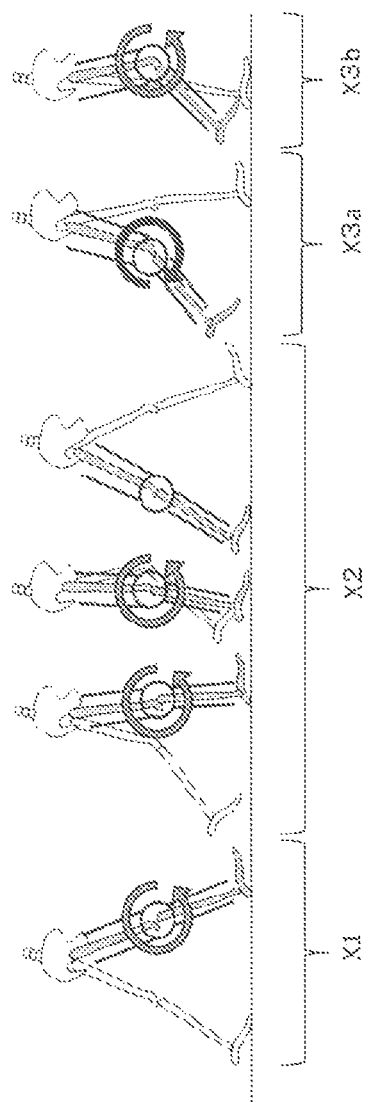
FIG. 20 is a schematic diagram showing a transition of gait postures during gait cycle.

FIG. 20 is a schematic diagram showing gait posture during gait cycle over time.

As shown in FIG. 20, a gait cycle includes a heel contact phase X1 including a heel contact time point when the heel contacts the ground in front of the vertical axis line (a period before and after the forward-raised foot contacts the floor), a stance phase X2 when the heel-contacted leg after heel contact is relatively moved backward while being in contact with the ground (a period when the floor-contacted lower leg is relatively moved backward relative to the body), an initial stage X3a of a swing phase when the lower leg of the leg contacting the ground since the end of the stance phase X2 is raised, and a later stage X3b of the swing phase when the raised lower leg is relatively moved forward and led to heel contact.

In the example shown in FIG. 19, the initial stage X3a of the swing phase is the reference gait motion timing (the zero point position of timing in FIG. 19) and, in this case, the heel contact phase X1 is in the vicinity of the position of timing 50%, and the stance phase X2 is at the position of timing 50% to 85%.

The reference gait motion timing can be set, for example, by measuring the lapse of a predetermined time from heel contact.

The timing of heel contact can be recognized by various methods.

For example, if the hip joint angular velocity when the thigh swings forward and backward based on the vertical axis line is referred to as positive and negative, respectively, the actuator-side control device can be configured to recognize as a heel contact timing a time point at which the calculated hip joint angular velocity advances by a predetermined phase angle Act from the timing (P0 in FIG. 17) at which the calculated hip joint angular velocity reaches zero from a positive value.

Alternatively, it is possible to provide the actuator unit 100 with a heel contact detecting means for detecting heel contact, and configure the thigh phase angle detecting means to recognize a timing detected by the heel contact detecting means as a heel contact time point and recognize the thigh phase angle φ at that timing as a heel contact phase angle.

When the acceleration sensor 515 is provided as in the actuator unit 100 of the gait motion assisting apparatus according to the present embodiment, the acceleration sensor 515 can also be used as the heel contact detecting means.

Alternatively, it is also possible to separately provide a pressure sensor capable of detecting ground contact of the heel and cause the pressure sensor to act as the heel contact detecting means.

Naturally, unlike the example shown in FIG. 19, it is also possible to regard the heel contact time point as the reference gait motion timing.

As the timing setting keys 620, the display part may be configured to display an assisting force start timing advancing-delaying key 625 and an assisting force end timing increase-decrease key 626 for respectively inputting an assisting force start timing and an assisting force end timing in place of, or in addition to, the assisting force start timing slider key 621 and the assisting force end timing slider key 622.

As shown in FIG. 19, in the present embodiment, the display part is configured to display, as the timing setting keys 620, the assisting force start timing slider key 621 and the assisting force end timing slider key 622 as well as the assisting force start timing advancing-delaying key 625 and the assisting force end timing increase-decrease key 626, and the assisting force start timing slider key 621 and the assisting force start timing advancing-delaying key 625 are linked to each other, and the assisting force end timing slider key 622 and the assisting force end timing increase-decrease key 626 are linked to each other.

The terminal-side control part 601 is configured to create, based on an assisting force setting value that is input into the touch panel 610, output pattern setting data indicating a relationship between a gait motion timing during gait cycle and the size of assisting force to be imparted to the lower frame 140 and save it in the tablet-side storage part 602. Then, when manual send operation is performed on the touch panel 610, the terminal-side control part 601 sends the output pattern setting data to the actuator-side control device 500 via the actuator-side wireless communication part 603.

In the present embodiment, as shown in FIG. 19, the display part is configured to display an application key 630, and when the application key 630 is operated, the terminal-side control part 601 sends to the actuator-side control device 500 the output pattern setting data that is based on an assisting force setting value input at that time.

Then, the actuator-side control device 500 is configured to overwrite-save, when receiving the output pattern setting data from the terminal device 600 (a tablet in the present embodiment), the output pattern setting data as the output pattern saved data.

This configuration enables the imparting timing of gait assisting force to be easily changed for each user and/or according to the extent of recovery of the user.

While the size (the output value and the output direction) of assisting force imparted during the assisting force imparting period can also be stored in the terminal-side control part 601 in advance, in the present embodiment, the size of assisting force can also be set by the terminal device 600 (a tablet in the present embodiment).

That is, in the present embodiment, the touch panel 610 is capable of receiving, in addition to the assisting force imparting period, the size (the output value and the output direction) of assisting force to be imparted during the assisting force imparting period as the assisting force setting value.

This configuration enables the output state of the driver 110 to be easily adjusted such that the driver 110 outputs gait assisting force having a necessary direction and a necessary output value for each user and/or according to the extent of recovery of the user.

Specifically, gait assisting force includes force for pushing the lower leg in the extending direction relative to the thigh and force for pushing the lower leg in the bending direction relative to the thigh, and the direction of necessary gait assisting force varies according to a motion timing during gait cycle.

For example, in the heel contact phase X1 and the stance phase X2, extending-direction gait assisting force for rotating the lower leg in the knee extending direction around the knee joint to prevent knee bending is necessary.

In the initial stage X3a of the swing phase, bending-direction gait assisting force for assisting the raising of the leg by rotating the lower leg around the knee joint in the knee bending direction is necessary.

In the later stage X3b of the swing phase, gait assisting force for rotating the lower leg around the knee joint in the knee extending direction is necessary.

In addition, whether gait assisting force is necessary in any or all of the four stages and/or what size of gait assisting force is necessary in a stage where gait assisting force is necessary varies for each user and/or according to the extent of recovery of the user.

In this regard, as in the present embodiment, a configuration, in which the size of assisting force can be input as the assisting force setting value via the touch panel 610 in addition to the assisting force imparting period, is effective.

In the present embodiment, the size of assisting force that can be input as the assisting force setting value include percentage relative to the predetermined reference output of the driver 110 and the output direction of the driver 110 indicating the rotational direction of the lower frame 140 around the actuator-side pivot axis line Y.

Specifically, the display part is configured to display an output setting key 640 for setting the output value and the output direction of gait assisting force.

In the present embodiment, as shown in FIG. 19, the display part is configured to display an output slider key 641 as the output setting key 640.

The output slider key 641 can be slidably operated between the "+100" position and the "−100" position, with the "0" position corresponding to the zero output of the driver 110 being in-between.

Here, + (plus) means that the output direction of the driver 110 is a direction in which the lower frame 140 is rotated toward one side around the actuator-side pivot axis line Y (e.g., a direction in which the lower leg is extended relative to the thigh), and − (minus) means that the output direction of the driver 110 is a direction in which the lower frame 140 is rotated toward the other side around the actuator-side pivot axis line Y (e.g., a direction in which the lower leg is bent relative to the thigh).

The display part may be configured to display, as the output setting key 640, an output increase-decrease key 645 for inputting the size of assisting force in place of, or in addition to, the output slider key 641.

As shown in FIG. 19, in the present embodiment, the display part is configured to display, as the output setting key 640, the output slider key 641 and the output increase-decrease key 645, and the output slider key 641 and the output increase-decrease key 645 are linked to each other.

Moreover, in the present embodiment, a plurality of waveform patterns of assisting force to be output by the driver 110 are saved in the terminal-side control part 601, and the touch panel 610 can be operated to select any waveform pattern from the plurality of waveform patterns.

Specifically, the display part is configured to display waveform pattern selecting keys 650 for selecting any waveform pattern from the plurality of waveform patterns. The terminal-side control part 601 creates output pattern setting data in which a period selected through a timing setting key 620 is used as a gait assisting force imparting period, an output value specified through the output setting key 640 is used as the size of gait assisting force, and a waveform pattern selected through a waveform pattern selecting key 650 is used as the output waveform of gait assisting force.

This configuration enables a user to be provided with more suitable gait assisting force.

In the embodiment shown in FIG. 19, four waveform patterns P1 to P4 can be selected, and the display part displays, as the waveform pattern selecting keys 650, first to fourth waveform pattern selecting keys 651 to 654 for selecting the waveform patterns P1 to P4, respectively.

The pattern P1 is an output pattern for gradually increasing the size of gait assisting force from the assisting force start timing to the assisting force end timing such that when the gait motion timing calculated based on the thigh phase angle φ reaches the assisting force start timing (87% in the example of FIG. 19), the output of gait assisting force is started, and when the gait motion timing calculated based on the thigh phase angle φ reaches the assisting force end timing (20% in the example of FIG. 19), the size of gait assisting force is at a set value (−100% in the example of FIG. 19).

The pattern P2 is an output pattern for gradually decreasing the size of gait assisting force from the assisting force start timing to the assisting force end timing such that when the gait motion timing calculated based on the thigh phase angle φ reaches the assisting force start timing (87% in the example of FIG. 19), the output of gait assisting force having a size corresponding to the set value (−100% in the example of FIG. 19) is started, and when the gait motion timing calculated based on the thigh phase angle φ reaches the assisting force end timing (20% in the example of FIG. 19), gait assisting force is zero.

The pattern P3 is an output pattern in which when the gait motion timing calculated based on the thigh phase angle φ reaches the assisting force start timing (87% in the example of FIG. 19), the output of gait assisting force having a size corresponding to the set value (−100% in the example of FIG. 19) is started, and this output is maintained until the assisting force end timing, and when the gait motion timing calculated based on the thigh phase angle φ reaches the assisting force end timing (20% in the example of FIG. 19), gait assisting force is terminated.

The pattern P4 is an output pattern in which when the gait motion timing calculated based on the thigh phase angle φ reaches the assisting force start timing (87% in the example of FIG. 19), the output of gait assisting force is started and increased to a set value (−100% in the example of FIG. 19) at a preset inclination, and when the gait motion timing calculated based on the thigh phase angle φ reaches a predetermined timing that is before the assisting force end timing (20% in the example of FIG. 19), the output of gait assisting force is started to be decreased, and gait assisting force is zero when the gait motion timing reaches the assisting force end timing (20% in the example of FIG. 19), wherein the inclination of gait assisting force is set such that gait assisting force during a period of 20% to 80% between the assisting force start timing and the assisting force end timing is at a set value (−100% in the example of FIG. 19).

Moreover, in the present embodiment, the terminal-side control part 601 is configured to divide-manage a gait cycle into a preset number n (n is an integer of 2 or greater) of output setting periods, and the touch panel 610 is capable of receiving an assisting force setting value for each of the n output setting periods.

Specifically, the display part is configured to display an output setting period selecting key 660 for selecting, from the first to $n^{th}$ output setting periods, one output setting period for which an assisting force setting value is input.

In the embodiment shown in FIG. 19, four output setting periods A1 to A4 are provided as the first to $n^{th}$ output setting periods, and the display part displays first to fourth period selecting keys 661 to 664 as the output setting period selecting key 660.

When any one output setting period of the first to $n^{th}$ output setting periods is selected by manual operation on the output setting period selecting key, the terminal-side control part recognizes that the selected one output setting period is in an editable state, and stores the values set through the timing setting key, the output setting key, and the waveform pattern selecting key at that time as output pattern setting data of said one output setting period recognized as being in an editable state.

This configuration enables n output patterns of gait assisting force to be set during gait cycle and a user to be provided with more suitable gait assistance.

In the present embodiment, the touch panel 610 is configured such that only the assisting force setting value of one or a plurality of (two or more and n or less) output setting periods selected from the n output setting periods can be reflected in the output pattern setting data.

Specifically, through the terminal device 600 (a tablet in the present embodiment), whether the input assisting force setting value is reflected in the output pattern setting data for each of the n output setting periods can be selected by manual operation on data reflection keys 670.

In the example shown in FIG. 19, the display part is configured to display an ON key 671 and an OFF key 672 as the data reflecting keys 670.

In this case, in a state where one output setting period is selected to be editable through an output setting period selecting key 660, the terminal-side control part 601 when the ON key 671 is operated causes the assisting force setting value of said one output setting period to be reflected in the output pattern setting data.

On the other hand, in a state where one output setting period is selected to be editable through an output setting period selecting key 660, the terminal-side control part 601 when the OFF key 672 is operated stores the assisting force setting value of said one output setting period but does not cause it to be reflected in the output pattern setting data.

In this case, when the output setting period in which the assisting force setting value is not reflected in the output pattern setting data by the operation of the OFF key 672 is selected through the output setting period selecting key 660 to be brought into an editable state again, and the ON key 671 is operated in this state, the terminal-side control unit 601 performs processing for reflecting the stored assisting force setting value of the output setting period in the output pattern setting data.

As shown in FIG. 19, in the present embodiment, the display part has an input key display area 611 for displaying input keys including the timing setting keys 620, the output setting key 640 and the waveform pattern selecting key 650, and a data display area 613 provided in an area different from the input key display area 611.

The display part is configured to display a graph of the output pattern setting data in the data display area 613.

In the example shown in FIG. 19, the displayed graph is a line graph.

This configuration enables a user to easily check the contents of the output pattern setting data at that time.

The graph depicted in FIG. 19 shows output pattern setting data in a state where the assisting force setting values of the A1 output setting period and the A2 output setting period are reflected in the output pattern setting data (i.e., an ON key 671-operated state), a state where the assisting force setting values of the A3 output setting period and the A4 output setting period are not reflected in the output pattern setting data (i.e., an OFF key 672-operated state), and a state where the assisting force setting value of the A1 output setting period has an assisting force start timing of 87%, an assisting force end timing of 20%, a gait assisting force setting value of −100%, and a waveform pattern of P3, and the assisting force setting value of the A2 output setting period has an assisting force start timing of 24%, an assisting force end timing of 40%, a gait assisting force setting value of +100%, and a waveform pattern of P3.

Preferably, the display part may be configured to display, among the plurality of output setting period selecting keys (four, i.e., A1 to A4, in the example of FIG. 19), a period selecting key for an output setting period that is currently selected and is in an editable state (the first period selecting key 661 in the example of FIG. 19) in a first color; among the plurality of output setting period selecting keys, a period selecting key for an output setting period that is not currently selected but for which an assisting force setting value is already input (the second period selecting key 662 in the example of FIG. 19) in a second color different from the first color; and among the plurality of output setting period selecting keys, period selecting keys for output setting periods for which the assisting force setting value is not yet input (third and fourth period selecting keys 663, 664 in the example of FIG. 19) in a third color different from the first and second colors.

This configuration enables whether an assisting force setting value is already input for each of the plurality of output setting periods to be easily checked.

As described above, while the terminal-side control part 601 is configured to send the output pattern setting data to the actuator-side control device 500 according to manual operation on the application key 630, and the actuator-side control device 500 is configured to overwrite-save, when receiving the output pattern setting data from the terminal device 600 (a tablet in the present embodiment), the output pattern setting data as the output pattern saved data, in the present embodiment, they are also configured to be capable of sending data in the opposite direction (i.e., sending data from the actuator-side control device 500 to the terminal device 600 (a tablet in the present embodiment)).

That is, as shown in FIG. 19, the display part is configured to display a read key 635, and the terminal-side control part 601 is configured to read, when the read key 635 is operated, output pattern saved data from the actuator-side control device 500 via the wireless communication parts 503, 603 and display the read output pattern setting data as a graph of output pattern setting data in the data display area 613.

This configuration makes it possible to easily confirm the assisting force setting value of the output pattern saved data being used by the actuator unit 100 at that time through the terminal device 600 (a tablet in the present embodiment), and also facilitate the work of creating new output pattern setting data by editing this output pattern saved data.

Preferably, the display part is configured such that when the output pattern setting data displayed in the data display area 613 is the same data as the output pattern saved data saved in the actuator-side control device 500, the graph is displayed in a first color, and when the output pattern setting data displayed in the data display area 613 is different from the output pattern saved data saved in the actuator-side control device 500, the graph is displayed in a second color different from the first color.

Specifically, at a stage where output pattern saved data is read from the actuator side control device 500 through the read key 635 and displayed in the data display area 613 as a graph, the output pattern data displayed in the data display area 613 is the same as the output pattern setting data stored in the terminal device 600 (a tablet in the present embodiment). Accordingly, in this state (a read and non-edited state), the graph is displayed in a first color.

When an input key (any of the timing setting keys 620, the output setting key 640, and the waveform pattern selecting key 650 in the example of FIG. 19) is operated in the read and non-edited state, the contents after operation are reflected in the graph displayed in the data display area 613. At this time, the contents of the output pattern setting data displayed in the data display area 613 are different from the contents of the output pattern saved data saved in the actuator-side control device 500. Accordingly, the displayed graph is changed from the first color to the second color.

Then, when the application key 630 is operated, thus the output pattern setting data of the terminal device 600 (a tablet in the present embodiment) is sent to the actuator-side control device 500, and the actuator-side control device 500 overwrite-saves the output pattern setting data as the output pattern saved data, the output pattern setting data displayed in the data display area 613 and the output pattern saved data saved in the actuator-side control device 500 have the same contents at that time. Accordingly, the displayed graph is returned from the second color to the first color.

This configuration enables the actuator unit 100 to be effectively prevented from being operated in an unintended assisting force set state, i.e., a state where the output pattern setting data displayed on the terminal device 600 (a tablet in the present embodiment) and the output pattern saved data saved in the actuator unit 100 are different from each other.

Reference number 680 shown in FIG. 19 indicates whether the terminal device 600 (a tablet in the present embodiment) and the actuator unit-side control device 500 are in a wirelessly communicable state, and reference number 682 is an operation stop key for turning the actuator unit 100 into an operation-off state from the terminal device 600 (a tablet in the present embodiment).

The terminal device 600 (a tablet in the present embodiment) is capable of saving an assisting force setting value after associating it with an ID and a password for each user, and is capable of causing the saved assisting force setting value to be displayed on the display part after receiving the ID and the password.

DESCRIPTION OF THE REFERENCE NUMERALS

1 Knee-ankle-foot orthosis
10 Thigh-side brace
30 Lower leg-side brace
100 Actuator unit
110 Driver
120 Upper frame
140 Lower frame
150 Actuator-side rotational connecting par
500 Actuator-side control device
510 Thigh orientation detecting means
600 Tablet terminal (terminal device)
601 Terminal-side control part
603 Terminal-side wireless communication part
610 Touch panel
611 Input key display area
613 Data display area
X Brace-side pivot axis line
Y Actuator-side pivot axis line

The invention claimed is:

1. A gait motion assisting apparatus comprising:
a terminal device; and
an actuator unit removably attachable to a knee ankle foot orthosis having a thigh-side brace and a lower leg-side brace to be respectively attached to a user's thigh and lower leg,
wherein the lower leg-side brace is connected to the thigh-side brace so as to be rotatable around a brace-side pivot axis line,
wherein the actuator unit has an upper frame and a lower frame respectively connectable to the thigh-side brace and the lower leg-side brace, an actuator-side rotational connecting part for connecting both frames such that the lower frame is rotatable around an actuator-side pivot axis line relative to the upper frame, a driver attached to the upper frame to produce driving force for rotating the lower frame around the actuator-side pivot axis line, a thigh orientation detecting means capable of detecting an angle-related signal relating to a hip joint angle that is a front-back swing angle of the user's thigh, and an actuator-side control device responsible for operational control for the driver,
wherein the actuator-side control device is configured to calculate, based on the angle- related signal at a sampling timing, a thigh phase angle at the sampling timing, calculate, based on the thigh phase angle, a gait motion timing during gait cycle corresponding to the sampling timing, apply the gait motion timing of the sampling timing to output pattern saved data that is saved in the actuator-side control device and that indicates a relationship between a gait motion timing during gait cycle and a size of assisting force to be imparted to the lower frame to calculate assisting force to be imparted to the lower frame at the sampling timing, and execute operational control for the driver such that the assisting force is output,
wherein the terminal device has a display part, an input part, a terminal-side control part, and a wireless communication part for performing wireless communication with the actuator-side control device, and is capable of receiving via the input part an assisting force setting value including an assisting force imparting period obtained by specifying a period for imparting assisting force to the lower frame by using a gait motion timing during gait cycle,
wherein the terminal-side control part creates, based on the assisting force setting value received via the input part, output pattern setting data indicating a relationship between a gait motion timing during gait cycle and a size of assisting force to be imparted to the lower frame, and sends the output pattern setting data to the actuator-side control device via the wireless communication part according to manual send operation via the input part, and
wherein the actuator-side control device overwrite-saves the output pattern setting data received from the terminal device as the output pattern saved data.

2. The gait motion assisting apparatus according to claim 1, wherein the terminal device is capable of receiving via the input part a size of assisting force to be imparted during the assisting force imparting period in addition to the assisting force imparting period as the assisting force setting value.

3. The gait motion assisting apparatus according to claim 2, wherein the size of assisting force that can be input as the assisting force setting value includes an output value specified in percentage relative to a predetermined reference output value of the driver and an output direction of the driver indicating a rotational direction of the lower frame around the actuator-side pivot axis line.

4. The gait motion assisting apparatus according to claim 2, wherein:
a plurality of waveform patterns of assisting force to be output by the driver are saved in the terminal-side control part,
the terminal device enables one waveform pattern to be selected from the plurality of waveform patterns via the input part, and
the assisting force setting value includes the waveform pattern selected via the input part.

5. The gait motion assisting apparatus according to claim 1, wherein:
the terminal-side control part is configured to divide-manage a gait cycle into a preset number n (n is an integer of 2 or greater) of output setting periods, and
the terminal device is capable of receiving an assisting force setting value for each of the n output setting periods via the input part.

6. The gait motion assisting apparatus according to claim 5, wherein the terminal device enables one or a plurality of output setting periods in which the assisting force setting value is reflected in the output pattern setting data to be selected from the n output setting periods via the input part.

7. The gait motion assisting apparatus according to claim 1, wherein the display part has an input key display area for displaying an input key for performing manual operation and a data display area for displaying a graph of the output pattern setting data.

8. The gait motion assisting apparatus according to claim 7, wherein the terminal-side control part reads output pattern saved data from the actuator-side control device via the wireless communication part according to manual read operation via the input part, and displays a graph of the output pattern saved data as output pattern setting data in the data display area.

9. The gait motion assisting apparatus according to claim 1, wherein:
the assisting force imparting period is a period defined by an assisting force start timing and an assisting force end timing specified in percentage relative to a gait cycle under a condition where a preset reference gait motion timing during gait cycle is regarded as a zero point, and
the output pattern setting data is data indicating a relationship between percentage of a gait motion timing relative to a gait cycle in a state where the reference gait motion timing is regarded as a zero point and a size of assisting force to be imparted to the lower frame.

10. The gait motion assisting apparatus according to claim 1, wherein the terminal device is a tablet terminal including a touch panel acting as the display part and the input part.

* * * * *